United States Patent [19]

Boyes et al.

[11] 4,218,477

[45] Aug. 19, 1980

[54] PRIMARY AMINOACYLANILIDES, METHODS OF MAKING THE SAME AND USE AS ANTIARRHYTHMIC DRUGS

[75] Inventors: Robert N. Boyes, Auburn; Benjamin R. Duce, Westborough; Emil R. Smith, Shrewsbury; Eugene W. Byrnes, Holden, all of Mass.

[73] Assignee: Astra Pharmaceutical Products, Inc., Worcester, Mass.

[21] Appl. No.: 651,420

[22] Filed: Jan. 22, 1976

Related U.S. Application Data

[60] Continuation-in-part of Ser. No. 442,775, Feb. 15, 1974, abandoned, Division of Ser. No. 321,590, Jan. 8, 1973, abandoned, which is a continuation-in-part of Ser. No. 107,031, Jul. 28, 1971, abandoned, and a continuation-in-part of Ser. No. 424,116, Dec. 12, 1973, abandoned, which is a continuation-in-part of Ser. No. 321,590, Jan. 8, 1973, abandoned, and Ser. No. 321,800, Jan. 8, 1973, abandoned, each is a continuation-in-part of Ser. No. 167,031, Jul. 28, 1971, abandoned.

[51] Int. Cl.$^2$ .................................................. A61K 31/165
[52] U.S. Cl. ................................ 424/324; 260/562 N
[58] Field of Search ............................................ 424/324

[56] References Cited

U.S. PATENT DOCUMENTS

| | | | |
|---|---|---|---|
| 2,794,835 | 6/1957 | Löfgren | 260/562 |
| 3,136,691 | 6/1964 | Nordstrom et al. | 424/324 |
| 3,542,850 | 11/1970 | Jansen et al. | 260/471 |
| 3,574,749 | 4/1971 | Howe et al. | 260/562 |

FOREIGN PATENT DOCUMENTS 705460  3/1954  United Kingdom .

OTHER PUBLICATIONS

Harrison et al., C.A., vol. 70, (1969), 113793z.
Hollunger, Acta Pharmucol. et Toxicol., 1960, 17, pp. 365-373.
Schöenberger et al., Archiv der Pharmazie, vol. 301, pp. 780–785, (1968).
Koelzer et al., C.A., vol. 55, (1961), 20171e.
Cilag. C.A., vol. 50, (1956), 4210e.
Cilag. C.A., vol. 51, (1957), 5117e.
Cilag. C.A., vol. 51, (1957), 5842i-5843a.

*Primary Examiner*—Allen J. Robinson
*Attorney, Agent, or Firm*—Brumbaugh, Graves, Donohue & Raymond

[57] ABSTRACT

Primary amino acylanilides of the formula

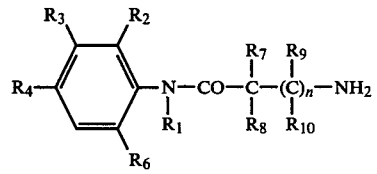

wherein $R_1$ is selected from the group consisting of hydrogen, methyl, ethyl and propyl, $R_2$ is selected from the group consisting of methyl, ethyl, chlorine, methoxy and ethoxy, $R_3$ is selected from the group consisting of hydrogen and methyl, $R_4$ is selected from the group consisting of hydrogen, methyl, and a $C_1$-$C_4$ alkoxy group, $R_6$ is selected from the group consisting of methyl, ethyl, chlorine, methoxy and ethoxy, $R_7$ is hydrogen, methyl or ethyl, $R_8$ is hydrogen, $R_9$ is hydrogen, methyl or ethyl, $R_{10}$ is hydrogen, and n is 0 or 1, with the provisions that (a) when n is 0, $R_8$ can also be methyl;
(b) when n is 1, and $R_7$ is hydrogen, and $R_9$ is hydrogen or methyl, then $R_{10}$ can also be methyl;
(c) when $R_1$ is hydrogen, $R_2$ is methyl, $R_3$ is hydrogen, $R_6$ is methyl, $R_7$ is hydrogen, $R_8$ is hydrogen, and n is 0, then $R_4$ can be ethoxy or propoxy only;
(d) when $R_1$ is hydrogen, $R_2$ is methyl, $R_3$, $R_4$, $R_7$ and $R_8$ are hydrogen, and n is 0, then $R_6$ is methoxy, ethoxy, or ethyl only;

and the therapeutically acceptable salts thereof. Compounds of this type have been found to be effective longlasting cardiac antiarrhythmic agents, especially when administered by the oral route.

51 Claims, No Drawings

PRIMARY AMINOACYLANILIDES, METHODS OF MAKING THE SAME AND USE AS ANTIARRHYTHMIC DRUGS

The application is a continuation-in-part of our co-pending applications Ser. No. 442,775 filed Feb. 15, 1974 and Ser. No. 424,116 filed Dec. 12, 1973, both now abandoned. Ser. No. 442,775 is a divisional application of Ser. No. 321,590 filed Jan. 8, 1973 which in turn was a continuation-in-part of Ser. No. 167,031 filed July 28, 1971, now both abandoned. Ser. No. 424,116 is a continuation-in-part of applications Ser. Nos. 321,590 and 321,800 filed Jan. 8, 1973, now both abandoned, which in turn were continuation-in-part applications of Ser. No. 167,031 filed July 28, 1971, now abandoned.

The present invention relates to primary acylanilides which have been shown to be effective as antiarrhythmic agents.

A number of anilides structurally distinct from those described herein are known. Some have been described in the literature as possessing therapeutic utility: Swedish Pat. Nos. 147,308; 147,309 and 153,705; Swiss Pat. Nos. 318,077; 336,815 and 464,882; German Pat. No. 967,642; French Pat. No. 1,161,363; British Pat. Nos. 705,460; 726,080; 754,413 and 809,286; 42 *Chemical Abstracts* 7871d (1948); 47 *Chemical Abstracts* 1055 g (1958) and U.S. Pat. No. 3,542,850.

Ever since the introduction of intensive coronary care, there has been emphasis on the treatment of ventricular extrasystoles and other cardiac arrhythmias. No conventional drug is completely satisfactory for control of such arrhythmias. Such drugs as quinidine, procainamide, propranolol and diphenylhydantoin (phenyltoin, Brit. Pharm.) have been used but exhibit undesirable side effects. Certain phenoxy derivatives of aminopropane have also been studied but their action on the central nervous system is similar to those of phenyltoin. *Proceedings of the British Pharmacological Society*, Vol. 39, p. 183, (1970).

In addition to the above-mentioned compounds, other pharmaceutical preparations exhibit antiarrhythmic properties. For example, the local anesthetic, Xylocaine (lidocaine), whose chemical name is 2-diethylamino-2′,6′-acetoxylidide, is an antiarrhythmic drug which is suitable for use intravenously or intramuscularly, Parkinson, P. I., et al., *Brit. Med. J.*, Vol. 2, pp. 29–30, (1970) and *The Merck Index*, 8th Ed., (Merck & Company, Inc., Rahway, New Jersey, 1968), P. 618, but is not orally effective due to low levels of the drug in the blood, Eisinger and Hellier, Lancet, 1969, II, 1303 and Boyes et al., *Clin. Pharmacol. Therap.* 12, No. 1, pp. 105–116 (1971). When lidocaine is administered orally there is a pronounced loss of the drug, probably due to the functions of the liver, through which most of the drug has to pass immediately following absorption from the intestinal tract. The duration of those blood levels obtained with lidocaine is also fairly short thereby precluding long duration of protection.

It is also known that certain 2-aminotetralins exhibit antiarrhythmic properties. D. M. Graeff et al., *Journal of Medicinal Chemistry*, Vol. 14, pp. 60–62 (1971).

The present invention comprises the use of primary amino acylanilides of the general formula

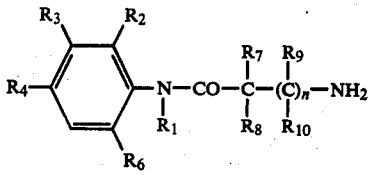

therapeutically acceptable salts thereof, and optical antipodes thereof as antiarrhythmic agents, wherein $R_1$ is selected from the group consisting of hydrogen, methyl, ethyl and propyl, $R_2$ is selected from the group consisting of methyl, ethyl, chlorine, methoxy, ethoxy, $R_3$ is selected from the group consisting of hydrogen and methyl, $R_4$ is selected from the group consisting of hydrogen, methyl, or a $C_1$–$C_4$ alkoxy group, $R_6$ is selected from the group consisting of methyl, ethyl, chlorine, methoxy and ethoxy, $R_7$ is hydrogen, methyl or ethyl, $R_8$ is hydrogen, $R_9$ is hydrogen, methyl or ethyl, $R_{10}$ is hydrogen and n is 0 or 1, with the provisions that
 (a) when n is 0, $R_8$ can also be methyl;
 (b) when n is 1, $R_7$ is hydrogen, and $R_9$ is hydrogen or methyl, then $R_{10}$ can also be methyl;
 (c) when $R_1$ is hydrogen, $R_2$ is methyl, $R_3$ is hydrogen, $R_6$ is methyl, $R_7$ is hydrogen, $R_8$ is hydrogen, and n is 0, then $R_4$ can be methyl, ethoxy, propoxy or butoxy only;

As illustrative examples of the meanings of the radicals $R_1$, $R_2$, $R_3$, $R_4$, $R_6$, $R_7$, $R_8$, $R_9$ and $R_{10}$ may be mentioned:

$R_1$: H, $CH_3$, $C_2H_5$, n-$C_3H_7$, iso-$C_3H_7$. Of these meanings, H, $CH_3$, $C_2H_5$ and n-$C_3H_7$ are preferred. Particularly preferred is H.

$R_2$: $CH_3$, $C_2H_5$, Cl, $OCH_3$, $OC_2H_5$. Of these meanings, $CH_3$, $C_2H_5$ and Cl are preferred. $CH_3$ and $C_2H_5$ are particularly preferred.

$R_3$: H, $CH_3$. Of these meanings, H is preferred.

$R_4$: H, $CH_3$, $OCH_3$, $OC_2H_5$, $OCH_2CH_2CH_3$, $OCH(CH_3)_2$, $O(CH_2)_3CH_3$,

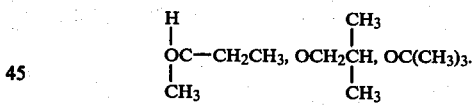

Of these meanings, H, $CH_3$, $OCH_2CH_2CH_3$, $O(CH_2)_3CH_3$ are preferred.

$R_6$: $CH_3$, $C_2H_5$, Cl, $OCH_3$, $OC_2H_5$. Of these meanings, $CH_3$, $C_2H_5$ and Cl are preferred.

$R_7$: H, $CH_3$, $C_2H_5$. Of these meanings H and $CH_3$ are preferred.

$R_8$: H, and, in some instances $CH_3$. Hydrogen is preferred.

$R_9$: H, $CH_3$, $C_2H_5$. Of these meanings, H and $CH_3$ are preferred.

$R_{10}$: H and, in some instances, $CH_3$. Hydrogen is preferred. The integer n can be either 0 or 1.

As examples of preferred combinations of radicals can be mentioned:
When n is 0:
 (a) $R_3=R_4=H$, $R_2=R_6=CH_3$.
 (b) $R_3=R_4=H$, $R_2=CH_3$, $R_6=Cl$.
 (c) $R_1=H$, $R_7=R_8=CH_3$.
 (d) $R_1=H$, $R_2=R_6=CH_3$, $R_3=R_4=H$, $R_7=H$ or $CH_3$, $R_8=H$ or $CH_3$.
When n is 1:

(e) $R_2=R_6=CH_3$, $R_3=R_4=H$.
(f) $R_2=CH_3$, $R_6=Cl$, $R_3=R_4=H$.
(g) $R_1=H$, $R_2=R_6=CH_3$, $R_3=R_4=H$, $R_7=R_8=H$, $R_9=H$ or $CH_3$, $R_{10}=H$ or $CH_3$.
(h) $R_1=H$, $R_7=R_8=H$, $R_9=R_{10}=CH_3$.

It is obvious that for certain combinations of $R_7$, $R_8$, $R_9$, $R_{10}$ and n the compounds of the formula I (including 2-amino-2',6'-propionoxylidide) exist in different stereoisomeric forms (optical isomers or antipodes). Such forms may be obtained by conventional methods, for instance the d- and l-optical isomers may be prepared by treatment of the corresponding racemate with l- and d-tartaric acids.

The present invention also comprises the primary aminoacylanilides of the general formula

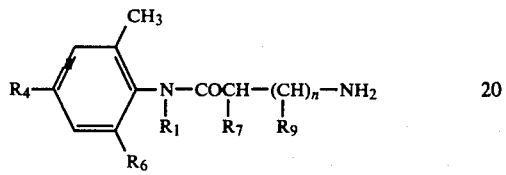

wherein $R_6$ is either methyl or ethyl, $R_4$ is hydrogen, methyl, propoxy or butoxy, $R_1$ and $R_7$ are both either hydrogen, methyl, or ethyl, $R_9$ is either hydrogen or methyl and n is either 0 or 1, provided that when $R_6$ is methyl, and $R_1$ and $R_7$ are also hydrogen, and n is also 0, then $R_4$ is propoxy. The therapeutically acceptable salts of the above compounds are included within the scope of the invention. The invention also comprises the use of the primary aminoacylanilides covered by the general formula depicted as antiarrhythmic agents wherein R groups are selected from the same group of organic radicals identified above and n is either 0 or 1 with the sole proviso that when $R_6$ is metyl and $R_4$, $R_1$ and $R_7$ are all hydrogen, then n is not 0. Pharmaceutical preparations containing such compounds also form a part of the present invention. These compounds are useful as long-lasting oral agents for the treatment of cardiac arrhythmias.

The following novel compounds are preferred embodiments of the invention:

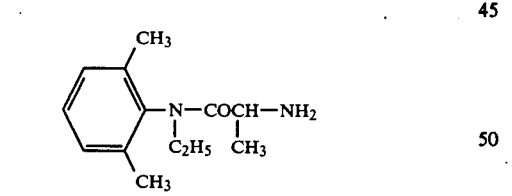
2-amino-N-ethyl-2',6'-propionoxylidide

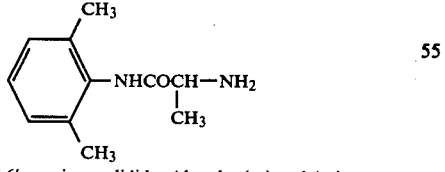
2-amino-2',6'-propionoxylidide. Also the (+) and (−) optical isomers.

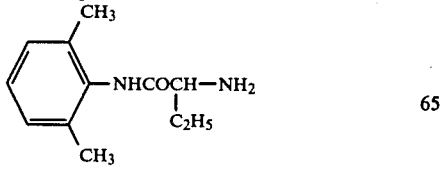
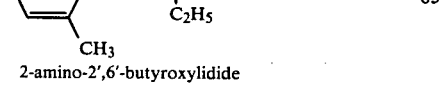
2-amino-2',6'-butyroxylidide

-continued

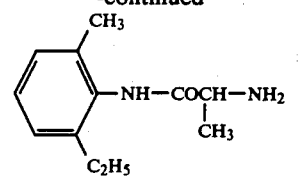
2-amino-2'-ethyl-6-'-methylpropionanilide

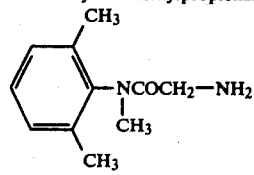
2-amino-N-methyl-2',6'-acetoxylidide

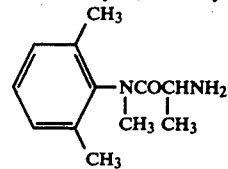
2-amino-N-methyl-2',6'-propionoxylidide

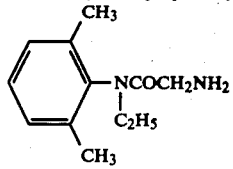
2-amino-N-ethyl-2',6'-acetoxylidide

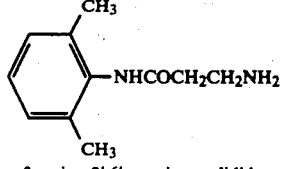
3-amino-2',6'-propionoxylidide

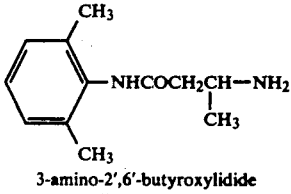
3-amino-2',6'-butyroxylidide

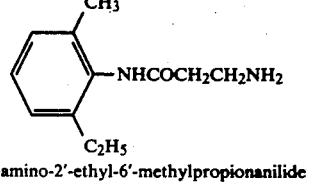
3-amino-2'-ethyl-6'-methylpropionanilide

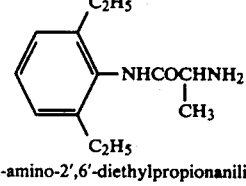
2-amino-2',6'-diethylpropionanilide

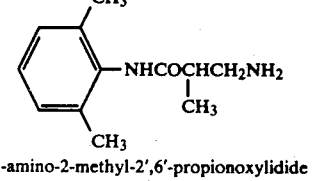
3-amino-2-methyl-2',6'-propionoxylidide

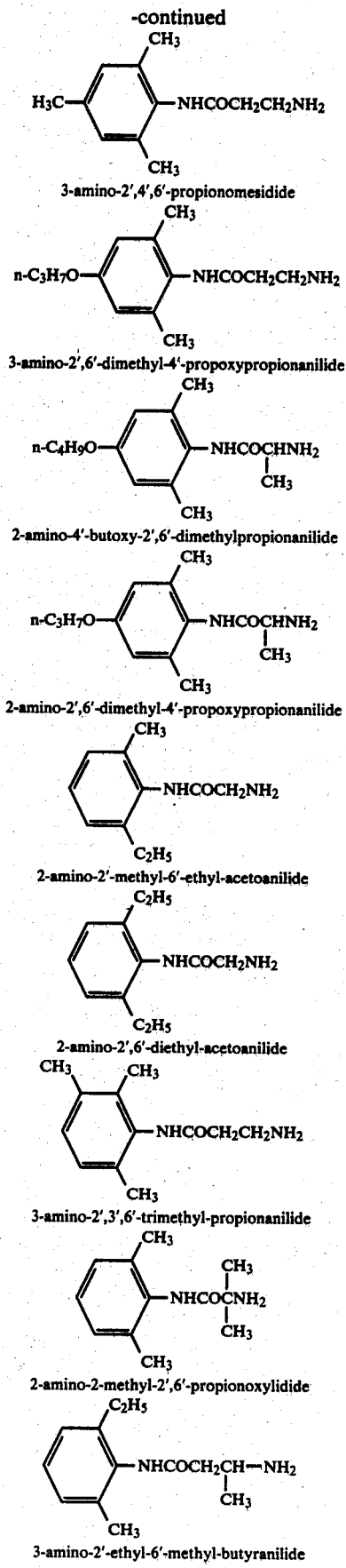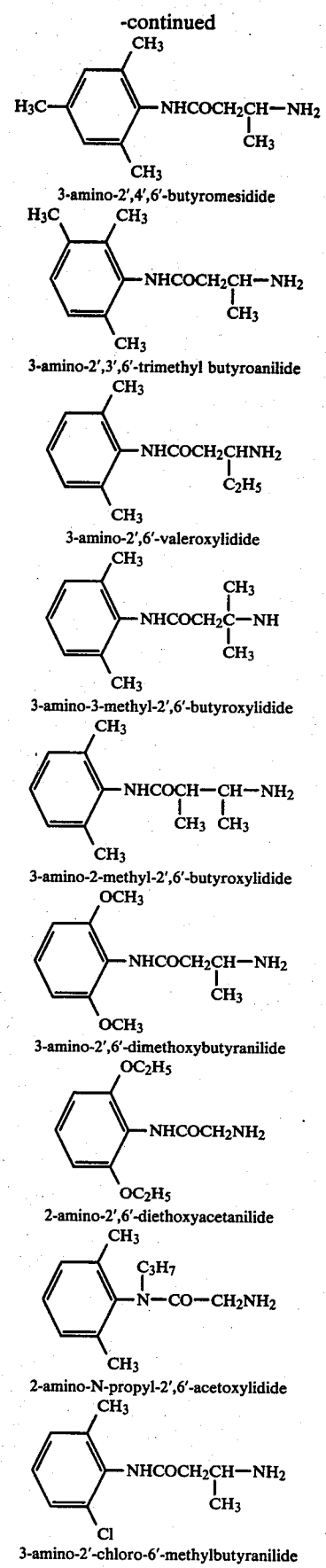

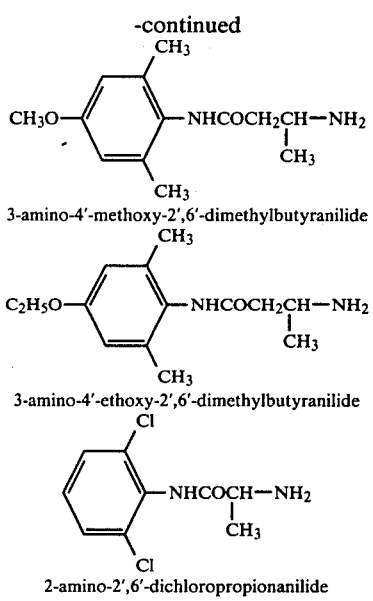

3-amino-4'-methoxy-2',6'-dimethylbutyranilide 3-amino-4'-ethoxy-2',6'-dimethylbutyranilide 2-amino-2',6'-dichloropropionanilide The expression "therapeutically acceptable salt" which is used herein is recognized in the art to designate an acid addition salt, which is physiologically innocuous when administered in a dosage and at an interval (e.g. frequency of administration) that is effective for the indicated therapeutic use of the parent compound. Typical therapeutically acceptable acid addition salts of the compounds listed above include, but are not limited to, the salts of mineral acids such as hydrochloric, phosphoric or sulphuric acid, and of organic acids, such as succinic and tartaric acids, and sulphonic acids, such as methane sulphonic acid.

In clinical practice the derivative of the invention will normally be administered orally or by injection in the form of pharmaceutical preparations comprising the active ingredient in the form of the free base or one of the common therapeutically acceptable salts, e.g., the hydrochloride, in association with a pharmaceutically acceptable carrier which may be a solid, semi-solid or liquid diluent or an ingestible capsule. Usually the active substance will comprise between 0.1% and 10% by weight of the preparation as, for example, in a water solution in the form of its soluble acid salt, although when present in the form of solid preparations, i.e., tablets or capsules, the concentration of the compounds of the claimed invention may be present up to 100% by weight of the tablet or capsule.

Pharmaceutical preparations in the form of dosage units for oral application may be formed by mixing either the base or acid salt form with a solid, pulverulent carrier. Examples are lactose, saccharose, sorbitol, mannitol, and starches such as potato starch, corn starch or amylopectin, cellulose derivatives, and gelatin. The carrier may also be lubricants such as magnesium or calcium stearate, a Carbowax or other polyethylene glycol wax compressed to form tablets or cores which can then be coated with either a concentrated sugar solution which may also contain gum arabic, gelatin, talcum and/or titanium dioxide, or which may be coated alternatively with a lacquer dissolved in a readily volatile organic solvent or mixture of organic solvents. Dyestuffs can be added to these coatings. Sustained release tablets are obtained by using several layers of the active drug, separated by slowly dissolving coatings. Another way of preparing sustained release tablets is to divide the dose of the active drug into granules with coatings of different thicknesses, and compress the granules into tablets together with the carrier substance. The active substance can also be incorporated in slowly-dissolving tablets made from fat and wax substance, or it may be evenly distributed in a tablet or an insoluble substance, such as a physiologically inert plastic substance as described in Fryklof et al. U.S. Pat. No. 3,317,394.

Soft gelatin capsules (pearl-shaped closed capsules) and other closed capsules consist, for example, of a mixture of gelatin and glycerol, and can contain mixtures of the active substance with a vegetable oil. Hard gelatin capsules contain granulates of the active substance with solid, pulverulent carriers such as lactose, saccharose, sorbitol, mannitol, or starches such as potato starch, corn starch or amylopectin, or cellulose derivatives or gelatin, as well as magnesium stearate or stearic acid.

For parenteral application by injection the preparations of the invention advantageously comprise an aqueous solution of a water-soluble, pharmaceutically acceptable acid salt of the active substance and optionally also contain a stabilizing agent and/or a buffer substance. The solutions may be made isotonic by the addition of sodium chloride.

In clinical use, the amount of active substance to be administered to the patient must be carefully adjusted depending on the individual requirements in each case. However, as illustrative examples of suitable dosage requirements in the treatment of acute states of ventricular arrhythmia may be mentioned administration of 3-amino-2',6'-butyroxylidide hydrochloride from about 100 mg. to about 1000 mg. by the intravenous route in a 70–80 kg. weight man. Orally administered daily requirements could be in the range from about 0.8 g. to about 8 g. The dosage unit of the compounds of the invention is at least 10 mg in the case of tablets, capsules and similar solid dosage forms, preferentially in the range of 50 to 500 mg.

The compounds listed above can be prepared in one or several of the following ways. Of the methods I–VII given below, the method VI can be used for the preparation of all compounds of the invention. The methods I–V and VII are not all applicable for the preparation of all compounds of the invention. The applicability of each of these methods can easily be determined by the skilled worker. All radical designations in the formulae are the same as given above unless stated otherwise. The term "Product" indicates the compounds of the present invention.

I. The reaction between a halogenacylanilide and ammonia in alcohol or in an alcohol-water mixture

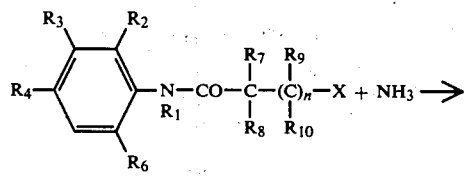

Product + HX

X is Cl, Br, I or a group known to react in a manner similar to those halogens, e.g. p-toluenesulfonyloxy, i.e. p-CH$_3$-C$_6$H$_4$-SO$_3$.

II. The Gabriel reaction

I.e. reaction between a chloro-, bromo-, or iodo-acylanilide and a suitable phthalimide salt to form an N-substituted phthalimide which is reacted with hydrazine to yield an intermediate that is decomposed by heating with acid:

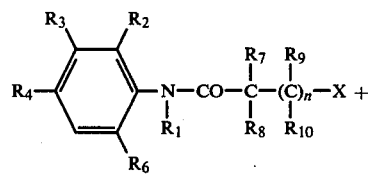

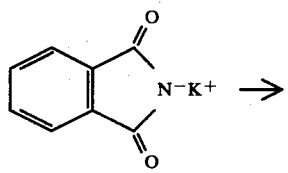

The "suitable phthalimide salt" is e.g. the potassium salt or any other suitable salt known to the art. The hydrazine may be used e.g. in the form of its hydrate or in the form of any other suitable derivative.

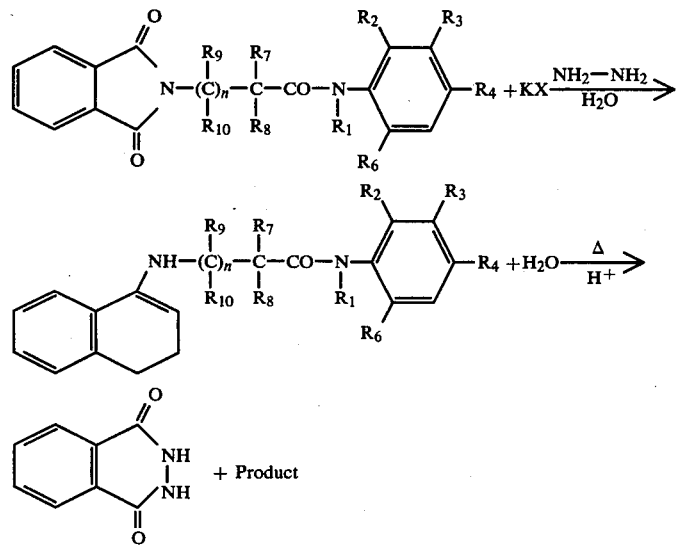

III. Addition of ammonia to an anilide of an unsaturated carboxylic acid [n = 1]:

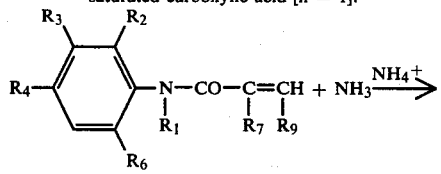

Product where n = 1 and R$_8$ and R$_{10}$ are both hydrogen.

IV. Reduction or hydrogenation of a cyanoacylanilide:

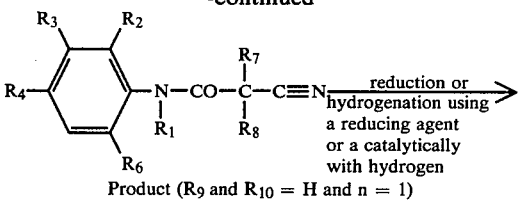

Product (R$_9$ and R$_{10}$ = H and n = 1)

V. Reaction of an aminoacid or an aminoacylhalogenide, the amino group of which is carrying a protecting group (P), and an aniline to form an intermediate compound from which the protecting group is separated to yield the desired amine

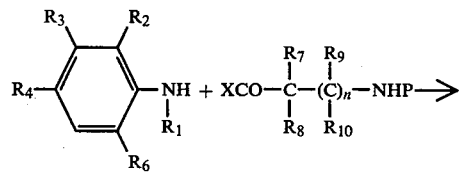

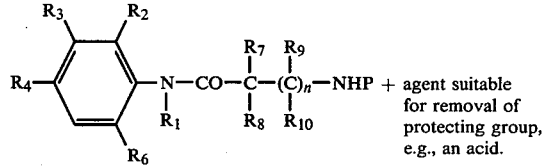

⟶ Product

The radical X is selected from the group consisting of hydroxy, chlorine and bromine. This method can be used for the preparation of all compounds of the invention.

The following are preferred methods for forming certain compounds of the present invention or represent intermediate processes useful in the synthesis of other similar compounds:

EXAMPLE 1

Synthesis of 2-amino-2',6'-propionoxylidide from 2-bromo-2',6'-propionoxylidide

The compound 2-amino-2',6'-propionoxylidide was synthesized by saturating with gaseous ammonia at room temperature a suspension of 50 grams (0.195 mole) of 2-bromo-2',6'-propionoxylidide in a mixture of 500 milliliters of 95% alcohol and 400 milliliters of concentrated aqueous ammonia. The saturation was carried out under mechanical stirring. After 25 hours the mixture was resaturated with ammonia gas. The stirring at room temperature was continued for a total period of 116 hours, and a sample was taken at that time. Gas chromatographic analysis indicated that about 95% of the bromo-compound had been converted to the desired product. The solvents were evaporated in vacuo, and the residue was taken up in 80 milliliters of 3 molar hydrochloric acid. After addition of 220 milliliters of water, the insoluble material was filtered off, was washed with 100 milliliters of water and was then dried. The insoluble material weighed 9.5 grams and was mainly unreacted bromo-compound. The filtrate was reacted with 50 milliliters of 7 molar NaOH, was extracted three times with methylene chloride (50 ml+2×25 ml portions), was dried over potassium carbonate, and then was evaporated. The yield of residue was 26.8 grams which corresponds to 71.4% of the theoretical yield. This residue was a colorless solidifying oil, and was dissolved in 200 ml chloroform. Hydrogen chloride was bubbled in until a sample of the solution tested acidic to wet pH indicator paper. A precipitate was obtained and was recovered by filtration. It was washed with chloroform and was dried. Its melting point was determined to be from 246° C. to 247.5° C. Gas chromatographic analysis of the material showed only one component. The calculated values for 2-amino-2',6'-propionoxylidide hydrochloride ($C_{11}H_{17}ClN_2O$ with molecular weight=228.5) are: C, 57.8; H, 7.49; N, 12.2; Cl, 15.5; and the values found upon analysis were: C, 57.7; H, 7.69; N, 12.2; Cl, 15.5. Infrared analysis (KBr disc, hydrochloride) showed: $\upsilon$ 2000–1850 (a broad band with shoulder, $NH_3+$), 1670 (amide I), 1540 (amide II), 1386, 1375 (symmetrical methyls), 760 $cm^{-1}$ (three adjacent hydrogens on phenyl).

EXAMPLE 2

Synthesis of 2-amino-2',6'-propionoxylidide from 2-chloro-2',6'-propionoxylidide.

In a one-liter bottle were mixed 17.5 g 2,6-xylidine and 123 ml glacial acetic acid and the mixture was cooled to 10°–15° C. A quantity of 20 g 2-chloropropionyl chloride was added and mixed rapidly followed immediately by a cooled (<10° C.) solution of 47.9 g sodium acetate trihydrate in 200 ml water. The contents were mixed at once and agitated for 30 min by mechanical shaking. The solid component was filtered and washed very carefully with distilled water. After drying, the 2-chloro-2',6'-propionoxylidide melted at 136.5°–137.5°. After recrystallization from 95% alcohol, it melted at 137°–138°. Analysis: Calcd. for $C_{11}H_{14}ClNO$: C 62.4, H 6.67, Cl 16.7. Found: C 62.3, H 6.74, Cl 16.6.

A mixture of 24.7 g 2-chloro-2',6'-propionoxylidide, 100 ml 95% ethanol, 75 ml concentrated ammonia and 0.12 g potassium iodide was placed in a pressure vessel and were saturated with gaseous ammonia at room temperature. The vessel was closed and kept at 75° C. for 96 hrs. After cooling, the contents were worked up as described in Example 1. The yield of 2-amino-2',6'-propionoxylidide was 89–97%.

EXAMPLE 3

Synthesis of 2-amino-2',6'-propionoxylidide from 2-iodo-2',6'-propionoxylidide.

A solution of 8.0 g sodium iodide was dissolved in 50 ml acetone and added to a warm solution of 9.5 g 2-bromo-2',6'-propionoxylidide in 50 ml acetone. After refluxing under stirring for one hour, the reaction mixture was cooled, and filtered from precipitated sodium bromide (3.8 g), and the filtrate was diluted with 300 ml of water. The precipitate was filtered off, washed carefully, and recrystallized from aqueous acetone and had a m.p. of 198.5°–199.5° C. The yield of 2-iodo-2',6'-propionoxylidide was almost quantitative. Calcd. for $C_{11}H_{14}INO$: C 43.6, H. 4.66, I. 41.9, H 4.62. Found: C 43.7, H 4.76, I 41.9, N 4.56.

A mixture of 11.4 g 2-iodo-2',6'-propionoxylidide, 145 ml 95% alcohol, and 76 ml concd. ammonia was saturated with gaseous ammonia and stirred at room temperature until no 2-iodo-2',6'-propionoxylidide could be shown to be present by gas chromatographic analysis. The reaction mixture was then worked up as described in Example 1. Yield of 2-amino-2',6'-propionoxylidide: 85–89%.

EXAMPLE 4 d- and l-isomers of 2-amino-2',6'-propionoxylidide

The racemic compound of 2-amino-2',6'-propionoxylidide was resolved into the d- and l-optical isomers by the following procedure:

The racemate of 2-amino-2',6'-propionoxylidide (51.9 g, 0.27 mole), dissolved in 95% ethanol (184 ml), was added to a hot clear solution of di-p-toluoyl-d-tartaric acid (104.3 g, 0.27 mole) in 95% ethanol (300 ml). An almost colorless precipitate formed which was filtered off after cooling (4° C.) for 48 hours and washed with a small amount of cold 95% ethanol and dried.

The precipitate was recrystallized from 95% ethanol until constant rotation was obtained ($[\alpha]_D^{23.5} = -114°$). An aqueous solution of the salt obtained was treated with 7M sodium hydroxide and the freed base extracted into methylene chloride. After drying ($K_2CO_3$), the solvent was evaporated leaving a solidifying oil (17 g) with $[\alpha]_D^{23} = -24.6°$.

The hydrochloride was prepared from a solution of the base in chloroform and gaseous hydrogen chloride. After recrystallization from absolute ethanol and ether (6:5), 17.7 g of the salt was obtained with a m.p. of 264°–265° (decomp.), $[\alpha]_D^{23} = -44.1°$.

The mother liquors obtained from the preparation and subsequent recrystallizations of the diastereomeric salt were combined, were evaporated, and were mixed with water and 7M sodium hydroxide to free the base. This was extracted exhaustively into methylene chloride and the combined extracts were dried ($K_2CO_3$), After evaporation, a solidifying oil (30.5 g) was obtained.

The base was dissolved in 95% ethanol (108 ml). To this solution was added di-p-toluoyl-l-tartaric acid (61.4 g, 0.159 mole), dissolved in 95% ethanol (176.6 ml). The formed precipitate was isolated from the cooled solution and recrystallized from 95% ethanol to constant rotation, $[\alpha]_D^{22.5} = +115°$. Yield: 34.9 g.

From the purified salt, the base and hydrochloride were prepared in a way analogous to that described above for the (−)-antipode. Thus was obtained 11.0 g of base with $[\alpha]_D^{23.5} = +24.9°$ and eventually 13.1 g of a hydrochloride melting at 264.5° C. (decom.) with a $[\alpha]_D^{26.5} = +43.7°$.

EXAMPLE 5

Synthesis of 2-amino N-methyl-2',6'-acetoxylidide.

Concentrated aqueous ammonia (30 ml, 0.459 mole) was added to a solution of 2-chloro-N-methyl-2',6'-acetoxylidide (10.0 g, 0.0474 mole) in 95% alcohol (20 ml) in a pressure vessel and heated to 75° C. for six hours. The reaction mixture was evaporated to dryness in vacuo. The residue was dissolved in water (50 ml) and brought to pH>10 with 7M NaOH whereupon the base was extracted with methylene chloride. The combined extracts were dried ($K_2CO_3$) and the solvent evaporated. From the residue (8.2 g, 90% yield), the d-tartrate was prepared by dissolving the residue in absolute ether and adding it to a solution of the equivalent amount of d-tartaric acid dissolved in absolute ethanol. The formed precipitate was filtered off, washed with absolute ether, and recrystallized from 95% alcohol. Mp. 173°–176° C. (decomp.) Calcd. for $C_{15}H_{22}N_2O_7$: C 52.6, H 6.48, N 8.18. Found: C 52.5, H 6.25, N 8.15.

EXAMPLE 6

Synthesis of 3-amino-2',6'-propionoxylidide.

A mixture of 3-bromo-2',6'-propionoxylidide (25.6 g, 0.10 mole), potassium phthalimide (20.3 g, 0.10 mole), and dimethylformamide (85 ml) was refluxed for two hours. When cool, a solution of 30 ml glacial acetic acid in 75 ml water was added, and the mixture was stirred for one hour. The solid was filtered off and dried, whereafter it was suspended in 95% alcohol (200 ml) and 85% aqueous hydrazine hydrate (9 ml, 0.28 mole) was added. The mixture was stirred and heated to reflux for two hours. Concd. hydrochloric acid (11 ml) was added, and the stirring was continued at room temperature for several hours. The solid was filtered off and washed with 95% alcohol. The filtrate was evaporated to circa 200 ml, cooled in an ice bath, and diluted to 1000 ml with ether. The precipitated hydrochloride was filtered off, redissolved in 150 ml absolute alcohol, filtered hot, and the cooled filtrate diluted with 550 ml ether. After cooling to 0° C., the hydrochloride was filtered off, washed with some ether, and dried. Yield: 18.2 g, (80%). Mp. 218°–221° C. Calcd. for $C_{11}H_{17}ClN_2O$: C 57.8, H 7.49, Cl 15.5, N 12.2. Found: C 57.7, H 7.48, Cl 15.7, N 12.1.

EXAMPLE 7

Synthesis of 3-amino-2',6'-butyroxylidide.

One gram of ammonium chloride was added to a solution of 2',6'-crotonoxylidide (11.8 g, 0.062 mole) in 95% alcohol (150 ml) and the mixture was saturated with gaseous ammonia at 0° C. The mixture thus prepared was placed in a pressure vessel and heated to 80° C. for 48 hours. The contents were transferred to a distillation until and the solvents were evaporated in vacuo leaving a solidifying oil as residue. This was dissolved in 1M HCl (75 ml) and extracted with ether. The ether was discarded. The acid solution was made alkaline with sodium hydroxide to pH 11. The liberated oily base was extracted exhaustively into methylene chloride. The combined extracts were dried ($K_2CO_3$), filtered, and concentrated in vacuo. An ethereal solution of hydrogen chloride was added and the formed precipitate of the hydrochloride (10.0 g) was collected and recrystallized from a mixture of alcohol and ether. The colorless crystals, dried for two hours at 0.1 mm Hg and 100° C., melted at 171°–173° C. Calcd. for $C_{12}H_{19}ClN_2O$: C 59.4, H 7.89, Cl 14.6, N 11.5. Found: C 59.3, H 8.10, Cl 14.4, N 11.4.

EXAMPLE 8

Synthesis of 2-amino-N-methyl-2',6'-propionoxylidide.

A solution of N-methyl-2,6-xylidine (19.4 g, 0.143 mole) in glacial acetic acid (123 ml) was cooled to 13° C. 2-bromopropionyl bromide (34.3 g, 0.160 mole) was added, mixed, and followed by a solution of sodium acetate trihydrate (47.8 g) in water (200 ml) previously cooled to 3° C. The ingredients were mixed and agitated for 30 min. Upon dilution with water (1000 ml), a precipitate formed which was filtered off, and was washed thoroughly with water and dried. Yield of 2-bromo-N-methyl-2',6'-propionoxylidide: 10.5 g, m.p.: 78.5°–80°.

The 2-bromo-N-methyl-2',6'-propionoxylidide thus prepared (10.0 g, 0.037 mole) was suspended in alcohol (50 ml) and concd. aqueous ammonia (40 ml) was added. The mixture was saturated with ammonia at 25° C. then heated to 50° C. under pressure. During this procedure, the disappearance of the 2-bromo-N-methyl-2',6'-propionoxylidide was followed gas-chromatographically. When practically all of this starting material had been reacted (48 hours), the solvents were evaporated in vacuo. The residue was dissolved in water (25 ml) with sufficient addition of 1M hydrochloric acid to make the solution acidic. The acid solution was extracted three times with ether. The ether was discarded and the acid solution was made alkaline with 7M sodium hydroxide and was saturated with potassium carbonate. The freed base was extracted into methylene chloride, and the combined extracts were dried ($K_2CO_3$), filtered, and the solution was saturated with gaseous hydrogen chloride. The solution was concentrated by evaporation to circa 45 ml volume and ether (50 ml) was added. A crystalline precipitate formed which was filtered off; Yield 8.68 g (97%), mp. 212°–214° C. (decomp.) Calcd. for $C_{12}H_{19}ClN_2O$: C 59.4, H 7.89, Cl 14.6, N 11.5. Found: C 59.2, H 7.73, Cl 14.5, N 11.5.

EXAMPLE 9

Synthesis of 2-amino-4'-n-butoxy-2',6'-dimethylpropionanilide.

A. Synthesis of 4-butoxy-2,6-dimethylazobenzene

To a solution of sodium (2.0 g, 0.09 mole) in absolute ethanol (119 ml) was added 2,6-dimethyl-4-hydroxyazobenzene (18.3 g, 0.08 mole) prepared according to B. C. Saunders and G. H. R. Watson, *Biochem. J.* 46:629–233 (1950). To the resulting orange-red solution was added 1-bromobutane (22.3 g, 0.162 mole) slowly from a separatory funnel and the mixture was refluxed for five hours. When cool, the precipitated sodium bromide was filtered off and the filtrate was evaporated to dryness. The residue was taken up in ether and the ether solution was extracted, first with 0.5 M sodium hydroxide and then once with water. The ether phase was dried ($Na_2$-

$SO_4$), filtered, and evaporated to dryness. The yield was over 90%. This material is satisfactory for the next step. After recrystallization from 95% ethanol, it melted at 47°–47.5° C. Calcd. for $C_{18}H_{22}N_2O$: C 76.6, H 7.85, N 9.92. Found: C 76.7, H 7.84, N 9.86.

B. Synthesis of 4-butoxy-2,6-dimethylaniline.

To a flask fitted with reflux condenser and stirrer containing 4-butoxy-2,6-dimethylazobenzene (53.4 g, 0.189 mole) was added 50% aqueous ethanol (480 ml). The mixture was heated close to boiling with stirring and sodium hydrosulfite ($Na_2S_2O_4$, 121.4 g, 0.697 mole) was added in small portions over a period of 30 min. The mixture was refluxed for 75 min. Most of the alcohol was distilled off and the oily amine layer formed in the operation was taken up in ether. The aqueous phase was made alkaline with sodium hydroxide and was extracted with ether. All the combined ether extracts were dried ($Na_2SO_4$), were filtered, and all low-boiling components were evaporated at reduced pressure (solvent and aniline), after which the residue was fractionated by distillation in vacuo. The fraction boiling at 105°–108° (0.1 mm Hg) was collected. Yield: (63%); $n_D^{25}=1.5337$. [Cf. E. Honkanen, Ann. Acad. Sci. Fennicae, Ser. AII, 99 (1960)].

C. Synthesis of 2-bromo-4'-butoxy-2',6'-dimethylpropionanilide.

In a two liter bottle were mixed 4-butoxy-2,6-dimethylaniline (50.7 g, 0.263 mole) and glacial acetic acid (224 ml) and the mixture was cooled to about 10° C. To this was added and mixed rapidly 2-bromopropionyl bromide (62.4 g, 0.289 mole) immediately followed by a precooled (5° C.) solution of sodium acetate trihydrate (87.2 g) in water (362 ml). The whole was vigorously shaken to ensure intimate mixture of the components. After 30 min. of mechanical shaking, the precipitate was filtered off and washed carefully with distilled water. It was thereafter dried. The yield was 68.9 g (72%). Recrystallized from 95% ethanol, it melted at 135.5°–136°. Calcd. for $C_{15}H_{22}BrNO_2$: C 54.9, H 6.75, Br 24.3. Found: C 55.1, H 6.22, Br 24.7.

D. Synthesis of 2-amino-4'-butoxy-2',6'-dimethylpropionanilide.

A mixture of 2-bromo-4'-butoxy-2',6'-dimethylpropionanilide (14.0 g, 0.0426 mole), 95% alcohol (109 ml) and concentrated aqueous ammonia (87 ml) was saturated with gaseous ammonia at room temperature and under continuous stirring. The dissappearance of the bromo-compound was followed gas chromatographically. Upon completion of reaction, the solvents were evaporated and the residue was stirred two hours at room temperature in a mixture of 3M hydrochloric acid (50 ml) and water (400 ml). The undissolved material was filtered off and the filtrate was extracted with ether. The ether was discarded, and the aqueous solution was made alkaline to pH 11 with 7M NaOH and was extracted exhaustively with methylene chloride. The combined extracts were dried ($K_2CO_3$), filtered, and the solvent was evaporated yielding an amber colored oil (9.3 g, 82%). This was converted to the hydrochloride with gaseous hydrogen chloride in ether. After recrystallization from alcoholether (1:1), it melted at 225°–6° C. Vacuum drying at elevated temperature (2 mm Hg, 100° C.) caused a reduction in weight of the obtained hydrochloride monohydrate. Calcd. for the hydrochloride monohydrate, $C_{15}H_{27}ClN_2O_3$: $H_2O$; 5.65. Found: $H_2O$; 5.90. Calcd. for the anhydrous hydrochloride $C_{15}H_{25}ClN_2O_2$: C 59.9, H 8.38, Cl 11.8, N 9.31. Found: C 59.7, H 8.48, Cl 11.8, N 9.25.

EXAMPLE 10

Synthesis of 2-amino-2',6'-butyroxylidide.

A mixture of 35.0 g 2-bromo-2',6'-butyroxylidide, 300 ml 95% alcohol and 300 ml concd. ammonia was saturated by gaseous ammonia, contained in a pressure vessel and heated to 60°–65° C. for 24 hours. The solvents were evaporated in vacuo, and the residue was dissolved in 200 ml of 1.5 M HCl. After filtering the solution was made alkaline to pH 11 with 7M NaOH and was extracted with ether three times. The combined ether extracts were dried ($K_2CO_3$), and the solvent was evaporated in vacuo. The yield was 21.5 g (80%). The residue was dissolved in a mixture of ether and chloroform (2:1), and the hydrochloride was prepared by addition of ethereal hydrogen chloride. After recrystallization from ethanol-butanone (1:1), it melted at 213.5°–214.5° C. Calcd. for $C_{12}H_{19}ClN_2O$: C 59.4, H 7.89, Cl 14.6, N 11.5 Found: C 59.3, H 7.83, Cl 14.5, N 11.4.

EXAMPLE 11

Synthesis of 3-amino-2'-ethyl-6'-methylpropionanilide.

A. Synthesis of 3-bromo-2'-ethyl-6'-methylpropionanilide.

In a glass-stoppered bottle, a solution of 2-ethyl-6-methylaniline (15.0 g, 0.111 mole) in glacial acetic acid (95 ml) was cooled to 13° C. and 3-bromo-propionyl chloride (21.1 g, 0.122 mole) was added. The mixture was mixed and was combined immediately with a cooled (3° C.) solution of sodium acetate trihydrate (36.9 g) in water (150 ml). The mixture was shaken vigorously for 30 min. The white product that formed was filtered off, washed carefully with water, and dried. This product, i.e., 3-bromo-2'-ethyl-6'-methylpropionanilide (27.4 g, 91%), melted at 149°–150° C. and was sufficiently pure for the next step.

B. Synthesis of 3-amino-2'-ethyl-6'-methylpropionanilide.

The 3-bromo-2'-ethyl-6'-methylpropionanilide (13.5 g, 0.0500 mole) described above, potassium phthalimide (10.2 g, 0.0551 mole), and dimethylformamide (50 ml) were stirred under reflux for two hours. A mixture of glacial acetic acid (20 ml) and water (50 ml) was added with continued stirring until the mixture reached room temperature. The solid phthalimide derivative was filtered off, washed with water, and dried. The yield: 13.8 g (82.1%), m.p.: 208°–209.5° C. This product (13.8 g, 0.041 mole) was suspended in 250 ml alcohol and an amount of 85% hydrazine hydrate (4.0 ml) was added. The mixture was refluxed with stirring for two hours. Concentrated hydrochloric acid (8 ml) was added and the stirring was continued until the mixture reached room temperature. The solid was filtered off, was washed with some 95% ethanol, and was discarded. The solvents were evaporated from the filtrate and the residue was dissolved in water, was filtered, and made basic with 7M sodium hydroxide, and was extracted exhaustively with methylene chloride. The extracts were dried ($K_2CO_3$), were filtered, and gaseous hydrogen chloride was fed into the solution. The salt that was formed was filtered off, was washed with methylene chloride, and was dried (9.5 g), and was recrystallized from alcohol-ether. Yield of 3-amino-2'-ethyl-6'-methylpropionanilide: 7.35 g, m.p.: 215.5°–216° C. Calcd. for $C_{12}H_{19}ClN_2O$: C 59.4, H 7.89, Cl 14.6, N 11.5. Found: C 59.3, H 7.80, Cl 14.6, N 11.7.

EXAMPLE 12

Synthesis of 2-amino-2',6'-dimethyl-4'-n-propoxypropionanilide.

A. Synthesis of 2,6-dimethyl-4-propoxyazobenzene.

To a solution of sodium (2.0 g) in absolute alcohol (120 ml) was added 2,6-dimethyl-4-hydroxyazobenzene (18.3 g) and 1-bromo propane (20 g). The mixture was refluxed for three hours and was left overnight at room temperature. A precipitate of sodium bromide was filtered off, was washed with some cold absolute ethanol, and was discarded. The alcohol was removed from the filtrate by distillation, the residue was dissolved in ether (200 ml), and was extracted with 2% sodium hydroxide solution (4×50 ml) and once with water. After drying ($Na_2SO_4$) and filtering, the ether solution was evaporated to dryness leaving a residual oily material (20.2 g), sufficiently pure for the following reaction step.

B. Synthesis of 2,6-dimethyl-4-propoxyaniline.

The yield of 2,6-dimethyl-4-propoxyazobenzene (20.2 g) from the previous step was dissolved in 95% alcohol (175 ml). Water was added (160 ml) and the mixture was heated to reflux. Sodium hydrosulfite ($Na_2S_2O_4$) (44.8 g) was added to the boiling solution in small portions. After completion of this addition, reflux was continued for 30–60 min. The alcohol was removed by distillation at reduced pressure. The remaining heterogeneous residue was made alkaline and was extracted with ether. The ether extract was dried ($Na_2SO_4$), filtered, and evaporated. The residual oil was fractionated by distillation in vacuo. After a forerun of aniline, the desired product distilled at 101° C. (0.7 mmHg); $n_D^{25}=1.5393$. The yield of 2,6-dimethyl-4-propoxyaniline was 6.86 g (51%). Calcd. for $C_{11}H_{17}NO$: C 73.7, H 9.56, O 8.93. Found: C 73.3, H 9.82, O 8.76.

C. Synthesis of 2-bromo-2',6'-dimethyl-4'-propoxypropionanilide.

This compound was prepared analogously with the corresponding p-butoxy homolog of Example 9C. A yield of 88% of the crude compound was obtained. After recrystallization from methanol, it melted at 147.5°–148° C. Calcd. for $C_{14}H_{20}BrNO$: C 53.5, H 6.41, Br 25.4. Found: C 53.6, H 6.32, Br 25.4.

D. Synthesis of 2-amino-2',6'-dimethyl-4'-propoxypropionanilide.

This compound was prepared in the same manner as 2-amino-4'-butoxy-2',6'-dimethylpropionanilide of Example 9D. The yield of crude base was 94% which was converted to the hydrochloride and recrystallized from absolute alcohol-ether; m.p. 226°–227° C. Calcd. for $C_{14}H_{23}ClN_2O_2$: C 58.6, H 8.08, O 11.2. Found: C 58.8, H 8.08, O 11.2.

EXAMPLE 13

Synthesis of 2-amino-2'-ethyl-6'-methylpropionanilide.

A. Synthesis of 2-bromo-2'-ethyl-6'-methylpropionanilide.

To a two-phase system, containing an aqueous sodium hydroxide solution (20 g sodium hydroxide in 200 ml water) and a mixture of 13.5 g 2-ethyl-2-methylaniline and 75 ml toluene (cooled to 8° C.), was added dropwise with stirring 25 g 2-bromopropionyl bromide. After this addition, stirring was continued for 15 min. and the formed crystals were filtered off. (Addition of petroleum ether to the filtrate precipitates more product, which can be added to the first crop). Total yield: 22.8 g (84%). After recrystallization from ether-petroleum ether, it melted at 181°–182° C.

B. Synthesis of 2-amino-2'-ethyl-6'-methylpropionanilide.

A slurry of 20.9 g 2-bromo-2'-ethyl-6'-methyl propionanilide, 125 ml 95% alcohol, and 75 ml concd. ammonia was saturated with gaseous ammonia and was heated to 55° C. for 30 hours in a pressure vessel. The reaction mixture was filtered and the filtrate concentration in vacuo. The residue was dissolved in 2M hydrochloric acid and was extracted with ethyl acetate. The acid phase was made alkaline to pH 9 and was extracted with methylene chloride to give 15.5 g of a crystallizing oil. Recrystallized from ether-petroleum ether, the compound (2-amino-2'-ethyl-6'-methylpropionanilide) melted at 68.5°–70° C. Calcd. for $C_{12}H_{18}N_2O$: C 69.8, H 8.79, N 13.6. Found: C 69.7, N 8.72, N 13.5.

EXAMPLE 14

Synthesis of 2-amino-N-ethyl-2',6'-acetoxylidide.

A mixture of 34.6 g crude 2-chloro-N-ethyl-2',6'-acetoxylidide (prepared analogously to Example 13A from chloroacetyl chloride and N-ethyl-2,6-xylidine), 450 ml ethanol, and 650 ml concd. aqueous ammonia was treated as described in Example 13B. The hydrochloride was prepared from an ethereal solution of the obtained crude yellowish oily base and hydrogen chloride. The salt was recrystallized from a mixture of methylene chloride-ethyl acetate and melted at 173.5°–176° C. Yield of pure 2-amino-N-ethyl-2',6'-acetoxylidide: 29.2 g. Calcd. for the hydrochloride $C_{12}H_{19}ClN_2O$: C 59.3, H 7.88, N 11.6. Found: C 59.5, H 8.03, N 11.5.

EXAMPLE 15

Synthesis of 3-amino-2',4',6'-propionomesidide.

This compound was prepared in a manner analogous to that described for 3-amino-2'-ethyl-6'-methylpropionanilide in Example 11B from 13.5 g 3-bromo-2',4',6'-propionomesidide, 10.2 g potassium phthalimide in 50 ml dimethylformamide by refluxing for 3 hours. The intermediate phthalimide derivative weighed 14.5 g (90% yield). This derivative was decomposed as described in Example 11B to give the desired base which was converted to the hydrochloride by bubbling anhydrous hydrogen chloride into a chloroform solution of the base. After recrystallization from alcohol with a small addition of water it melted at 272.5°–273.5° C. Its $pka_a^{23}$ value was found to be about 8.7–8.8. Calcd. for $C_{12}H_{19}ClN_2O$: C 59.4, H 7.89, Cl 14.6, N 11.5. Found: C 59.2, H 7.78, Cl 14.5, N 11.6.

EXAMPLE 16

Synthesis of 3-amino-2',6'-dimethyl-4'-propoxypropionanilide.

A. Synthesis of 3-bromo-2',6'-dimethyl-4'-propoxypropionanilide.

This compound was prepared analogously to 3-bromo-2'-ethyl-6'-methylpropionanilide of Example 11A from 20 g 4-propoxy-2, 6-xylidine, 95 ml glacial acetic acid, 37 g sodium acetate trihydrate, 150 ml water 21.2 g 3-bromopropionyl bromide. The yield was 93% of recrystallized (methanol:water) material melting at 121.5°–122.5° C.

B. Synthesis of 3-amino-2',6'-dimethyl-4'-propoxypropionanilide.

This compound was prepared analogously to 3-amino-2'-ethyl-6'-methylpropionanilide of Example 11B from 15.7 g 3-bromo-2',6'-dimethyl-4'-propoxypropionanilide and 10.2 g potassium phthalimide in 50 ml dimethyl formamide. The intermediate phthalimide derivative was obtained in 88% yield. It was decomposed by being suspended in 250 ml 95% alcohol with addition of 4 ml of 64% hydrazine and refluxing for 90 min. A hydrochloride was prepared from the obtained base; m.p. 208°–210.5° C. Calcd. for $C_{14}H_{23}ClN_2O_2$: C 58.6, H 8.08, Cl 12.4, N 9.77. Found: C 58.8, H 8.20, Cl 12.3, N 9.96.

EXAMPLE 17

2-amino-2',3',6'-trimethylacetanilide.

A. 2-chloro-2',3',6'-trimethylacetanilide.

A mixture of 7.8 g of 2,3,6-trimethylaniline R. A. Scherrer and H. R. Beatty, J. Org. Chem. 37, 1681 (1972), and 50 ml glacial acetic acid was cooled to 10° C. in a glass stoppered bottle, 7.23 g chloroacetyl chloride was added, mixed quickly and followed immediately by a cooled solution of 19.3 g sodium acetate trihydrate in 80 ml water. The mixture was shaked for 30 min. and the solid material was filtered off and washed carefully with water. After drying, a yield of 9.94 g (81%) was obtained. It melted at 145°–146° C. Analysis: Calcd. for $C_{11}H_{14}ClNO$: C 62.4, H 6.67, Cl 16.8. Found: C 62.4, H 6.78, Cl 16.8.

B. 2-amino-2',3',6'-trimethylacetanilide.

A mixture of 9.74 g 2-chloro-2',3',6'-trimethylacetanilide, 9.45 g potassium phthalimide and 41 ml dimethylformamide was refluxed with mechanical stirring for two hours. To the mixture was added 16.4 ml glacial acetic acid diluted with 41 ml of water and the whole was warmed and stirred for 30 minutes. The solid was filtered off and dried yielding 13.9 g (94%) of the adduct with a melting point of 270°–271° C. The adduct was suspended in 75 ml 95% alcohol and 3.7 ml 85% aqueous hydrazine hydrate was added. The mixture was heated with vigorous stirring, 40 ml of 95% alcohol was added, and refluxing was continued for one hours. To the mixture was added 5.6 ml concd. hydrochloric acid and 40 ml 95% alcohol and stirring was continued while the mixture was cooling for 30 minutes. The solids were filtered off and the filter cake was slurried in water and filtered off. This procedure was repeated once. The combined filtrates (if necessary they can be refiltered) were evaporated and this left a residue of 9.5 g of material which was recrystallized from alcohol with addition of some water. The crystals melted at 283.5°–284.5° C. (decomp.). Analysis: Calcd. for $C_{11}H_{17}ClN_2O$: C 57.8, H 7.49, Cl 15.5, N 12.2. Found: C 57.7, H 7.50, Cl 15.4, N 12.4.

EXAMPLE 18

2-amino-2',6'-diethylacetanilide.

Using the method described in Example 8B, a mixture of 2-chloro-2',6'-diethylacetanilide (37.5 g, 0.166 mole), potassium phthalimide (33.8 g, 0.183 mole) and dimethylformamide (165 ml) were reacted to obtain 51.4 g (92% yield) of the phthalimide derivative (m.p. 243°–243.5° C.) from which the hydrochloride of the desired ompound was obtained, m.p. 269°–270° C. (abs. ethanol - abs. ether). Calcd. C 59.4, H 7.89, N 11.5, Cl 14.6. Found: C 59.2, H 7.75, N 11.7, Cl 14.8.

EXAMPLE 19

2-amino-2',6'-diethylpropionanilide.

A. 2-bromo-2',6'-diethylpropionanilide.

Following the procedure described in Example 8A using 2,6-diethylaniline and 2-bromopropionyl bromide the desired intermediate was obtained in 80% yield. Recrystallized from abs. methanol it melted at 197°–199° C. Calcd.: C 54.9, H 6.38, N 4.93, Br 28.1. Found: C 54.8, H 6.19, N 5.02, Br 27.9.

B. 2-amino-2',6'-diethylpropionanilide.

From the bromo compound described above and using the procedure of Example 10B the desired compound was obtained as the hydrochloride monohydrate in a yield of about 85%. On heating to 100° C. in high vacuum a weight loss corresponding to one mole of water per mole of hydrochloride monohydrate was obtained. Calcd. ($C_{13}H_{23}ClN_2O_2$): $H_2O$ 6.56. Found: $H_2O$ 6.83. The anhydrous hydrochloride gave the following analysis. Calcd. ($C_{13}H_{21}ClN_2O$): C 60.8, H 8.24, N 10.9. Found: C 60.7, H 8.22, N 10.9.

EXAMPLE 20

2-amino-2'-ethyl-6'-methylacetanilide.

The hydrochloride of this compound was obtained in 68% yield following the procedure described in Example 10B using 2-chloro-2'-ethyl-6'-methylacetanilide as starting material. Recrystallized from alcohol-ether the salt melted at 248°–250.5° C. Calcd. ($C_{11}H_{17}ClN_2O$): C 57.8, H 7.49, N 12.3, Cl 15.5. Found: C 57.5, H 7.58, N 12.1, Cl 15.7.

EXAMPLE 21

2-amino-N-ethyl-2',6'-propionoxylidide.

A. 2-bromo-N-ethyl-2',6'-propionoxylidide.

A two-phase system consisting of a solution of N-ethylxylidine (20.9 g, 0.14 mole) in toluene (100 ml) and a solution of potassium carbonate (40 g, 0.29 mole) in water (200 ml) was stirred vigorously and 2-bromopropionyl bromide (53.0 g, 0.245 mole) was added dropwise during 15 minutes keeping the temperature of the reaction mixture at 20° C. After continued stirring for 40 minutes at room temperature the product was separated by extraction with ethyl acetate. After evaporation of the solvents an almost quantitative yield of solidifying oil was obtained which would be recrystallized from petroleum ether, m.p. 64°–66° C.

B. 2-amino-N-ethyl-2',6'-propionoxylidide.

From the bromo compound described above, using the method of Example 10B, the hydrochloride of the desired compound was obtained in 81% yield. Recrystallized from ethanol-ethyl acetate it melted at 195°–6° C. Calcd. ($C_{13}H_{21}ClN_2O$): C 60.8, H 8.24, N 10.9, Cl 13.8. Found: C 60.6, H 8.30, N 10.8, Cl 14.1.

EXAMPLE 22

3-amino-2-methyl-2',6'-propionoxylidide.

A. 2-methyl-2',6'-acryloxylidide.

A Grignard reagent solution was prepared from magnesium (29.0 g, 1.2 moles), ethyl bromide (130 g, 1.2 moles) and 400 ml of abs. ether. Over a period of 45 min. 2,6-xylidine (121 g, 1.0 mole), dissolved in 400 ml. of abs. ether, was added with effective mechanical stirring. Another 400 ml of abs. ether was added followed by a solution of methyl methacrylate (100 g, 1.0 mole) in 400 ml. of abs. ether, added during 30 min. at reflux. Refluxing was continued for 2 hrs. The reaction mixture was cooled and 800 ml. of 9 N HCl was added slowly and carefully under continued stirring and cooling. The ether phase was separated, washed with water, 0.2 M sodium bicarbonate, and water, dried over anhydrous magnesium sulfate, and filtered. The ether was evaporated leaving a solid that could be recrystallized from petroleum ether (b.p. 60°–110°) containing a small amount of isopropyl alcohol or from a mixture of ethyl alcohol and water. Yield: 35%, m.p. 101°–105°.

B. 3-amino-2-methyl-2',6'-propionoxylidide.

This compound was obtained in a 59% yield from 2-methyl-2',6'-acryloxylidide (described above) following the method described in Example 4 with the differences that ammonium bromide was used instead of ammonium chloride and that the reaction mixture was heated to 115°–120° C. for four days. The final product was isolated and identified with IR and NMR spectroscopy.

EXAMPLE 23

Synthesis of 3-amino-2',6'-propionoxylidide.

2-cyano-2',6'-acetoxylidide N. Löfgren and C. Tegnér, Acta Chem. Scand. 9, 493–6 (1955) (5 g, 0.026 mole) in 50 ml 10% ethanolic ammonia is hydrogenated in a Parr shaker at 25°–40°→C. and a pressure of 2.5 atmospheres in the presence of 1 gram of rhodium-/alumina. After completed hydrogenation, the catalyst is filtered off and the filtrate evaporated to dryness. The residue is dissolved in ethanol and the hydrochloride is prepared by addition of gaseous hydrogen chloride. Complete precipitation of the salt is achieved by addition of ether. After filtering, the hydrochloride can be recrystallized from ethanolether and melts at 218°–221° C., and is identical to the product described in Example 3.

EXAMPLE 24

Synthesis of (+)-2-amino-2',6'-propionoxylidide.

Carbobenzoxy-L-alanine (4.50 g, 0.020 mole) and 2,6-xylidine (2.72 g, 0.0224 mole) were dissolved in 50 ml methylene chloride. Dicyclohexylcarbodiimide (4.6 g, 0.0223 mole) dissolved in 20 ml methylene chloride was added. The mixture was heated to the boiling point and allowed to cool to room temperature on the water bath. After another hour at room temperature, the precipitate was filtered, washed with a small portion of methylene chloride and dried; yield 4.38 g (97%) m.p. 228.5°–230.5° C. of the formed by-product diphenylurea. The filtrate was evaporated to dryness, and the residual colorless solid, weighing 6.69 g (102%) after drying, melted at 167°–169.5°.

An amount of the product thus obtained, N-(carbobenzoxy-L-alanyl)-2,6-xylidine, (3.25 g, 0.010 mole) was mixed with 25 ml absolute ethanol and 25 ml methylene chloride. Palladium on charcoal catalyst (1.0 g) was added and the mixture was hydrogenated in a Parr shaker at 48 psi. After about one hour, the catalyst was filtered off and the filtrate was evaporated. The residue was dissolved in 1 M hydrochloric acid (25 ml) and filtered. The filtrate was made alkaline with 7 M sodium hydroxide. The base was extracted into methylene chloride, the extraction being facilitated by saturating the aqueous phase with potassium carbonate. The combined extracts (15 ml) were dried over anhydrous potassium carbonate and diluted with 30 ml anhydrous ether. Hydrogen chloride was passed through the solution and the precipitated hydrochloride was filtered off and recrystallized from ethanol-ether; yielding 1.89 g colorless crystals. Repeated recrystallization gave a product melting at 264.5°–265.5° C. An amount of 0.2640 g dissolved in 10.0 ml methanol gave a specific rotation, $[\alpha]_D^{25}$, of +41.7° indicating a purity of at least 95%. The L-2-amino-2',6'-propionoxylidide obtained is thus identical to the (+)-antipode described in Example 1. A mixture of the product obtained and the (−)-enantiomer of Example 1 melted at 234°–251° showing an appreciable depression.

PHARMACEUTICAL PREPARATIONS

The following illustrate methods of formulation of the compounds of the invention for parenteral or oral administration:

EXAMPLE 25

Solutions of 3-amino-2',6'-butyroxylidide hydrochloride for injection.

| Ingredients | Amounts | |
|---|---|---|
| | 2% solution | 4% solution |
| 3-amino-2',6'-butyroxylidide, hydrochloride | 20 g | 40 g |
| sodium chloride | q.s. to obtain isotonicity | |
| hydrochloric acid (2N) | q.s. to obtain a pH of 4.0–4.2 | |
| sodium hydroxide (2N) | q.s. to obtain a pH of 4.0–4.2 | |
| distilled water for injection | q.s. to obtain 1000 ml solution | |

The solid ingredients are dissolved in 950–957 ml of distilled water for injection. Hydrochloric acid or sodium hydroxide solution is added until the pH is in the defined range. The solution is diluted to 1000 ml with distilled water for injection, filtered through a millipore membrane to obtain sterility and filled aseptically into sterile containers.

EXAMPLE 26

Liquid preparation for oral administration of 3-amino-2',6'-butyroxylidide hydrochloride.

A liquid preparation was prepared containing the following ingredients:
3-amino-2',6'-butyroxylidide hydrochloride: 30.0 g
Liquid glucose: 300 g Sucrose: 250 g
Preservative: q.s.
Flavor Essence: q.s.
Certified color: q.s.
Purified water: ad 1000 ml The therapeutic utility of the compounds disclosed herein is illustrated in the following examples:

Pharmacological Activity

EXAMPLE 27 considered as fibrillating if fine tremulous movements were present on the surface of the ventricle and persisted for at least 5 seconds after the thoracotomy or the mechanical stimulus. Ventricular fibrillation was considered absent in those animals in which coordinated ventricular activity was evident following such procedures.

Table I shows the comparative effects obtained by oral administration of lidocaine, quinidine, procainamide and 2-amino-2',6'-propionoxylidide:

TABLE I

| Acute oral toxocity and antifibrillatory effects in mice | | | Proportion of mice in each group | | | | | | Proportion of mice in each group having | | | | | |
|---|---|---|---|---|---|---|---|---|---|---|---|---|---|---|
| | | protected against fibrillation at $LD_{0.1}$ | ataxia just before $CHCl_3$ challenge | | | | | | | | | | | |
| 24 Hr. Mortality | | (Time of administration of drug before $CHCl_3$ challenge) | (Time of administration of drug before $CHCl_3$ challenge) | | | | | | | | | | | |
| | | (mg/kg) | (mins) | | | | | | 5 min | 10 min | 20 min | 40 min | 80 min | 160 min |
| Drugs | $LD_{50}$ | $LD_{0.1}$ | 5 | 10 | 20 | 40 | 80 | 160 | | | | | | |
| Quinidine* | 382 | 348 | — | — | 10/10 | 9/9 | 9/9 | — | — | — | 0/10 | 2/10+ 1 death | 9/9 (mild) +1 death | — |
| Procainamide** | 643 | 248 | 0/10 | 1/10 | 0/10 | — | — | — | 0/10 | 0/10 | 0/10 | — | — | — |
| Lidocaine** | 224 | 154 | — | 9/10 | 10/10 | 7/10 | 0/10 | — | — | 0/10 | 9/10 | 0/10 | 0/10 | — |
| 2-Amino-2',6'-propionoxylidide** | 529 | 382 | — | — | 9/10 | 9/10 | 10/10 | 9/10 | — | — | 10/10 | 10/10 | 8/10 | 5/10 |

*as sulfate salt
**as sulfate salt

The ability of one of the preferred compounds of the present invention, i.e., 2-amino-2',6'-propionoxylidide, to suppress cardiac arrhythmias has been demonstrated in both mice and dogs.

The experiments on mice were performed according to a modification of the method described by J. W. Lawson, "Antiarrhythmic activity of some isoquinoline derivatives determined by a rapid screening procedure in the mouse", *J. Pharm. Exp. Therap.* Vol. 160, pp. 22–31 (1968). This method is based upon the observation that when an unanesthetized, untreated mouse is exposed to chloroform vapor its respiration soon ceases and at that time both electrocardiographic and visual inspection reveal that the cardiac ventricles are fibrillating. If the mouse is treated appropriately with known antiarrhythmic agents prior to exposure to chloroform, the respiratory failure is not accompanied by ventricular fibrillation.

Groups of 10 female Swiss albino mice (HAM/ICR) each weighing 18 to 25 g. were pretreated with a dose (approximate $LD_{0.1}$—the dose to kill one of a thousand) of 2-amino-2',6'-propionoxylidide at 10, 20, 40, 80 and/or 160 minutes, respectively, before being placed in a 2000 ml beaker containing cotton and 50 ml of chloroform. Immediately after cessation of respiration each mouse was removed from the beaker, its thorax was opened and its heart was examined for the presence of absence of ventricular fibrillation. The nature of the cardiac rhythm was then confirmed by electrocardiographic recordings. Whenever fibrillation was not evident, the heart was touched with forceps. The heart was

EXAMPLE 28

Tests on dogs with the compound 2-amino-2',6'-propionoxylidide were conducted according to a modification of the method described by A. S. Harris in "Delayed Development of Ventricular Ectopic Rhythms Following Experimental Coronary Occlusions", Circ. Vol. 1, pp. 1318–1328 (1950). In this method the dogs were anesthetized, the heart was exposed, and the anterior descending branch of the left coronary artery was ligated in two stages. The thorax was closed and the dog was allowed to recover from the anesthesia. Throughout the first 2 to 3 days after such surgery, electrocardiograms have revealed the presence of ventricular arrhythmias and these arrhythmias have been shown to be suppressed by known antiarrhythmic agents. B. B. Clark and J. R. Cummings, "Arrhythmias Following Experimental Coronary Occlusion and Their Response to Drugs", *Annals New York Academy of Sciences,* Vol. 65, pp. 543–551 (1956). In order to test the effect that 2-amino-2',6'-propionoxylidide has upon these arrhythmias, unanesthetized dogs were supported in canvas slings and were treated either intravenously or orally with the drug. The electrocardiographic, cardiovascular and other drug effects were monitored. These experiments revealed that both oral and intravenous doses produced a distinct suppression of the ventricular arrhythmias unaccompanied by any discernible adverse reactions.

Table II summarizes the results of oral administration:

TABLE II

Response of Unanesthetized Dogs to Oral Doses of 2-amino-2',6'-propionoxylidide on the First Day after Coronary Artery Ligation. (Doses in aqueous solution were introduced into stomach through tube followed by 50 ml tap water.)

| CUMUL. Dose as HCl (mg/kg) oral | Dog NR. | Maximum Antiarrhythmic Activity | | | Overt Toxicity (Minutes after Treatment) | | | | | |
|---|---|---|---|---|---|---|---|---|---|---|
| | | Partial Clearing Onset + (mins.) | Complete Clearing* Onset (mins) | Duration** (mins) | Emesis | Tremors | Nystagmus | Convulsions Onset | Duration | Other |
| 50 | 215 | None | None | — | None | None | None | None | — | None |
|  | 220 | — | 15 | 195*** | None | None | None | None | — | None |
| 100 | 240 | — | 120 | 45 | None | None | None | None | — | None |
| 150 | 215 | — | 105 | <15 | 95 | None | None | None | — | None |
|  | 220 | — | 45 | >90 | None | None | None | None | — | None |
| 200 | 240 | — | 60 | 30*** | 2 | 45;68 | None | 45;68;73 | >3 | None |
|  | 225 | — | 15 | 30*** | 19;64;74 | None | None | None | — | None |
| 300 | 225 | — | 30 | >180 | None | None | None | None | 17 | None |

*Incidence of abnormal ventricular beats decreased to less than 5% of total beats.
**Return of 50% of suppressed abnormal ventricular beats.
***Followed by off and on bursts of abnormal ventricular beats.
+ A 50–95% reduction in the incidence of abnormal ventricular beats from the control values.
Ligation was performed near the distal edge of the left auricular appendage. A double ligature was passed under the freed artery and was cut, thereby giving two ligatures at the same position on the artery. The first was drawn snugly around the artery on a 20 gauge needle which was withdrawn. After 30 minutes the second ligature was tightened to close the artery.
Dogs #215 and #220 given 50 mg/kg dose at 0 mins and 100 mg/kg dose at 240 mins. Dog #225 given 200 mg/kg at 0 mins and 100 mg/kg at 180 mins. Dog #240 given 100 mg/kg at 0 mins and 100 mg/kg at 240 mins.

EXAMPLE 29

The response of unanesthetized dogs to intravenous infusion of 2-amino-2',6'-propionoxylidide and comparison with the response to lidocaine, on the first day after coronary artery ligation is given below in Table III. The dosage schedule was: 1st hr.: 15 mg/kg/hr; 2nd hr.: 30 mg/kg/hr; 3rd hr.: 60 mg/kg/hr. Infusions were stopped at the first sign of toxicity other than emesis.

TABLE III

| Item | Compound Tested | |
|---|---|---|
| | Lidocaine | 2-amino-2',6'-propionoxylidide |
| Dogs tested | 2 | 1 |
| Number of dogs showing antiarrhythmic effect* | 2 | 1 |
| Antiarrhythmic doses (cumul. mg/kg) | 36 & 55 | 75 |
| Duration of Antiarrhythmic effect (mins.)** | 5 & 5 | 71 |
| Toxic doses (cumul. mg/kg) | 55 & 70 | 81 |
| Max. Plasma Level of drug (μg/ml) | 10 & 15 | — |
| Approximate plasma $t^{\frac{1}{2}}$*** | 00 & 00 | — |

*Incidence of abnormal ventricular beats decreased to less than 5% of total beats.
**Return of 50% of suppressed abnormal ventricular beats.
***$t^{\frac{1}{2}}$ indicates the half life of the drug administered. 00 indicates that the amount of the drug in the blood plasma remains fairly constant per unit time.
Ligation was performed near the distal edge of the left auricular appendage. A double ligature was passed under the freed artery and was cut, thereby giving two ligatues at the same position on the artery. The first was drawn snugly around the artery on a 20 gauge needle which was withdrawn. After 30 minutes the second ligature was tightened to close the artery.

EXAMPLE 30

The antiarrhythmic effect of a number of the ether compounds of the present invention was likewise demonstrated by observing the protection they gave against chloroform induced fibrillation in mice. The procedure used was a modification of the method previously described. The modification involved using a standard time of 20 minutes for each test run and four different doses of the same drug. Route of administration was subcutaneous. A dose-response curve was constructed from these values and an $ED_{50}$ value thus obtained was compared to an $ED_{50}$ value for lidocaine as a standard. The relative potency is $ED_{50}$ test compound/$ED_{50}$ lidocaine. Test results are shown in Table IV.

Table IV

| Test Compound | Relative Potency* |
|---|---|
| 2-amino-2', 6'-propionoxylidide (racemate) | 0.33 (0.20 – 0.54) |
| 2-amino-2', 6'-propionoxylidide [(−)form] | 0.45 (0.26 – 0.78) |
| 2-amino-2', 6'-propionoxylidide [(+)form] | 0.11 (0.06 – 0.21) |
| 2-amino-2', 6'-dimethyl-4'-propoxypropionanilide | 0.61 (0.40 – 1.1) |
| 2-amino-4'-butoxy-2', 6'-dimethyl-propionanilide | 0.84 (0.48 – 1.5) |
| 3-amino-2'-ethyl-6'-methyl-propionanilide | 0.29 (0.09 – 0.81) |
| 2-amino-2'-ethyl-6'-methyl-propionanilide | ≈ 0.7 |
| 3-amino-2', 4', 6'-propionomesidide | 0.30 (0.20 – 0.6) |
| 3-amino-2', 6'-dimethyl-4'-n-propoxypropionanilide | 0.20 (0.12 – 0.34) |
| 2-amino-2', 6'-butyroxylidide | 0.35 (0.21 – 0.56) |
| 2-amino-N-methyl-2', 6'-propionoxylidide | 0.36 (0.24 – 0.52) |
| 2-amino-N-ethyl-2', 6'-propionoxylidide | 0.73 (0.44 – 1.0) |
| 2-amino-2'-ethyl-6'-methyl acetanilide | 0.27 (0.14 – 0.40) |
| 2-amino-2', 6'-diethylpropionanilide | 0.48 (0.27 –0.73) |
| 2-amino-N-methyl-2', 6'-acetoxylidide | 0.51 (0.19 – 1.3) |
| 2-amino-2', 6'-diethylacetanilide | 0.22 (0.13 – 0.36) |
| 3-amino-2', 6'-propionoxylidide | 0.4 (0.2 – 0.8) |
| 3-amino-2', 6'-butyroxylidide | 0.99 (0.60 – 1.9) |

*The value outside the parentheses indicates the statistical means. The figures within the parentheses are the confidence limits.

EXAMPLE 31

A number of the compounds of the present invention were tested to also measure the protection they give against chloroform induced fibrillation in the guinea pig. Guinea pigs (250–350 g) were placed individually into a series of 4000 ml beakers containing cotton and 100 ml of chloroform. After cessation of respiration the animal was removed from the beaker, the thorax was opened and the heart was examined for the presence or absence of ventricular fibrillation. The nature of the cardiac rhythm was confirmed by electrocardiographic recordings. Whenever fibrillation was not evident, the heart was touched with forceps. Fibrillation was considered present if fine tremulous movements were present on the surface of the ventricle and persisted for at least 5 seconds after the thoracotomy or the mechanical stimulus. Ventricular fibrillation was considered absent in those animals in which coordinated ventricular activity was evident following such procedures.

A single dose (about 1-5 ml) of each test compound was administered intraperitoneally by a 25 gauge needle twenty minutes before the animals were placed in chloroform.

Table V sets forth the protection observed with a variety of doses of test compounds:

Table V

| Test Compound | Dose (mg/kg) | Percent of Population Protected |
|---|---|---|
| 2-amino-N-methyl-2′, 6′-acetoxylidide | 328 | 100% |
|  | 165 | 90% |
| 3-amino-2′, 6′-butyroxylidide | 326 | 100% |
| 2-amino-N-methyl-2′, 6′-propionxylidide | 200 | 87% |
| 2-amino-2′, 6′-butyroxylidide | 63 | 50% |
| 3-amino-2′, 6′dimethyl-4′ propoxypropionanilide | 200 | 33% |

EXAMPLE 32

The compound 3-amino-2′,6′-butyroxylidide was also tested on dogs, according to a modification of the method of Harris as previously described. As in the previously described tests, unanesthetized dogs were supported in canvas slings and were treated either intravenously or orally with doses of 3-amino-2′,6′-butyroxylidide. The electrocardiographic, cardiovascular and other drug effects were monitored. These experiments revealed that both oral and intravenous doses produced a distinct suppression of the ventricular arrhythmias unaccompanied by any discernible adverse reactions.

Table VI summarizes the results of intravenous treatment with the drug, again confirming its antiarrhythmic effectiveness at doses with minimal toxic side-effects.

Table VI

| | Response of Unanesthetized Dogs to Intravenous Doses of 3-amino-2′, 6′-butyroxylidide on the First Day after Coronary Artery Ligation | | | | | | |
|---|---|---|---|---|---|---|---|
| | Severity of Arrhythmia | | Antiarrhythmias Activity | | | Toxicity | |
| Dog No. | Venticular Rate (beats/min) | % Ventricular Ectopics | Dose to Partial Clearing mg/kg | Dose to Total Clearing mg/kg | Duration min. | Convulsions | Deaths |
| 559 | 216 | 100 | 30 | 50 | 75 | None | None |
| 547 | 222 | 100 | 7.5 | 32 | 330 | None | None |
| 543 | 195 | 100 | 15 | 18 | 96 | None | None |
| 544 | 198 | 96 | 15 | 22 | 30 | None | None |

The compounds of the present invention unexpectedly demonstrate antiarrhythmic effects. They have a weak local anesthetic effect compared to lidocaine, a known anesthetic and antiarrhythmic drug. To demonstrate this, 20 mM solutions of 2-amino-2′,6′-propionoxylidide, one of the preferred compounds, and lidocaine were compared in vitro for their effect on the frog sciatic nerve according to the method of Camougis and Takman, "Nerve and Nerve-Muscle Preparations (As Applied to Local Anesthetics)", Chapter 1, in *Methods of Pharmacology*, A. Schwartz, ed., Appleton-Century-Crofts, New York, New York (1970). It was found that the lidocaine solution blocks the action potential of the nerve to the extent of 78% of the normal potential after 5 minutes, whereas 2-amino-2′,6′-propionoxylidide does not block the action potential at all even after exposure of the nerve to the solution for 96 min.

Despite the generally well-recognized teaching in the prior art that antiarrhythmic activity and local anesthetic activity are closely related and that primary amines are much less potent local anesthetics than the corresponding secondary amines, the weak local anesthetics of the present invention exhibit strong antiarrhythmic properties. A. P. Truant and B. Takman, "Local Anesthetics", *Drills, Pharmacology and Medicine*, J. R. DiPalma, ed., McGraw-Hill Book Co., New York, New York, (1965) and F. F. Doerge, "Local Anesthetic Agents", *Textbook of Organic Medicinal and Pharmaceutical Chemistry*, 5th Ed., by C. O. Wilson et al., Lippincott, Philadelphia, Pa., pp. 597–598 (1966).

The compounds of the present invention when administered to mammals do not produce methemoglobin in the animal's bloodstream. This is due to the type of substituents that these compounds have at the ortho-position of the benzene ring.

It has also been found that the primary amines of the present invention, when administered to treat mammals suffering from cardiac arrhythmias, cause significantly fewer side effects such as ataxia and convulsions, than are caused by the secondary amines which also cause these side effects. To demonstrate the superiority of the claimed compounds in reducing side effects, the primary amine of the invention, 2-amino-2′,6′-propionoxylidide, was compared with the secondary amine having the formula

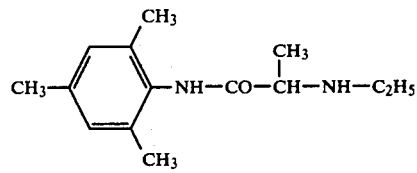

The incidence of ataxia and convulsions at the ED$_{50}$ dose level for protecting against chloroform-induced arrhythmias in mice was compared for the above two compounds. The ED$_{50}$'s, that does which will protect 50 percent of the test animals against chloroform-induced arrhythmias, for both compounds are approximately equal, 172 mg/kg for the primary amine and 162 mg/kg for the secondary amine. For the secondary amine, ataxia occurred in 100% of the test animals and convulsions occurred in 90%. For the primary amine of the invention, no ataxia occurred at doses above ED$_{50}$ (200 mg/kg) and convulsions were observed in only 34% of the test animals at 251 mg/kg. These results indicate that the claimed primary amines differ significantly from the secondary amines in producing undesirable side effects.

Other differences in the pharmacological activity of primary and secondary amines have been reported by Strong et al in *Clin. Pharm. and Therapeutics*, 14, (1), 1973 and by Blumer et al in *J. Pharm. and Exp. Therapeutics*, 186, (1), 1973.

A preferred embodiment of the invention, i.e., 2-amino-2',6'-propionoxylidide and its salts, has been found to provide antiarrhythmic effects when administered to dogs in oral doses of from 50 mg/kg to 100 mg/kg, and intravenously in a cumulative dose of 75 mg/kg, and to mice in a maximum oral dosage of about 380 mg/kg and should be effective for humans in a dosage of about 6 grams/day, orally.

We claim:

1. A process for the suppression of cardiac arrhythmias in mammals comprising administering to the mammal an amount effective for the suppression of cardiac arrhythmias of a compound selected from the group consisting of

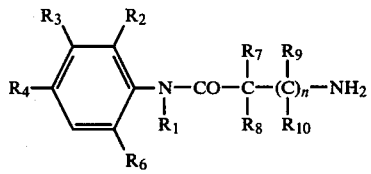

wherein $R_1$ is selected from the group consisting of hydrogen, methyl, ethyl, and propyl, $R_2$ is selected from the group consisting of methyl, ethyl, chlorine, methoxy, and ethoxy, $R_3$ is selected from the group consisting of hydrogen and methyl, $R_4$ is selected from the group consisting of hydrogen, methyl, and a $C_1$–$C_4$ alkoxy group, $R_6$ is selected from the group consisting of methyl, ethyl, chlorine, methoxy, and ethoxy, $R_7$ is selected from the group consisting of hydrogen, methyl and ethyl, $R_8$ is hydrogen, $R_9$ is selected from the group consisting of hydrogen, methyl and ethyl, $R_{10}$ is hydrogen, and n is 0 or 1, provided that when $R_1$ is hydrogen, $R_2$ is methyl, $R_3$ is hydrogen, $R_6$ is methyl, $R_7$ and $R_8$ are hydrogen, and n is 0, then $R_4$ can be methyl, ethoxy, propoxy, or butoxy only; the optically active isomers of such compounds as have an asymmetric carbon atom, and the therapeutically acceptable salts thereof.

2. A process for the suppression of cardiac arrhythmias in mammals comprising administering to the mammal an amount effective for the suppression of cardiac arrhythmias of a compound selected from the group consisting of:

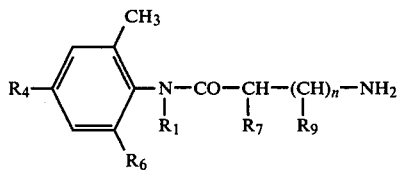

wherein $R_6$ is selected from the group consisting of methyl and ethyl, $R_4$ is selected from the group consisting of hydrogen, methyl, propoxy and butoxy, $R_1$ and $R_7$ are both selected from the group consisting of hydrogen, methyl and ethyl, n is an integer no larger than 1, and $R_9$ is selected from the group consisting of hydrogen and methyl, provided that when $R_6$ is methyl, and $R_4$, $R_1$ and $R_7$ are all also hydrogen, then n is not 0, and therapeutically acceptable salts thereof.

3. A process for the suppression of cardiac arrhythmias in mammals comprising administering to the mammal an amount effective for the suppression of cardiac arrhythmias of a compound selected from the group consisting of 2-amino-2',6'-propionoxylidide;
(+)-2-amino-2',6'-propionoxylidide;
(−)-2-amino-2',6'-propionoxylidide;
2-amino-N-ethyl-2',6'-propionoxylidide;
2-amino-2',6'-butyroxylidide;
2-amino-2'-ethyl-6'-methylpropionanilide;
2-amino-N-methyl-2',6'-acetoxylidide;
2-amino-N-methyl-2',6'-propionoxylidide;
2-amino-N-ethyl-2',6'-acetoxylidide;
3-amino-2',6'-propionoxylidide;
3-amino-2',6'-butyroxylidide;
3-amino-2'-ethyl-6'-methylpropionanilide;
2-amino-2',6'-diethylpropionanilide;
3-amino-2-methyl-2',6'-propionoxylidide;
3-amino-2',4',6'-propionomesidide;
3-amino-2',6'-dimethyl-4'-propoxypropionanilide;
2-amino-4'-butoxy-2',6'-dimethylpropionanilide;
2-amino-2',6'-dimethyl-4'-propoxypropionanilide;
2-amino-2'-methyl-6'-ethyl-acetonanilide;
2-amino-2',6'-diethyl-acetoanilide;
3-amino-2',3',6'-trimethyl-propionanilide;
2-amino-2-methyl-2',6'-propionoxylidide;
3-amino-2'-methyl-6'-ethyl-butyranilide;
3-amino-2',4',6'-butyromesidide;
3-amino-2',3',6'-trimethyl-butyroanilide;
3-amino-2',6'-valeroxylidide;
3-amino-3-methyl-2',6'-butyroxylidide;
3-amino-2-methyl-2',6'-butyroxylidide;
3-amino-2',6'-dimethoxybutyranilide;
2-amino-2',6'-diethoxyacetanilide;
2-amino-N-propyl-2',6'-acetoxylidide;
3-amino-2'-chloro-6'-methylbutyranilide;
3-amino-4'-methoxy-2',6'-dimethylbutranilide;
3-amino-4'-ethoxy-2',6'-dimethylbutyranilide,
2-amino-2',6'-dichloropropionanilide, and therapeutically acceptable salts thereof.

4. The process according to claim 3 which comprises administering 2-amino-2',6'-propionoxylidide or a therapeutically acceptable salt thereof.

5. The process according to claim 3 which comprises administering (+)-2-amino-2',6'-propionoxylidide or a therapeutically acceptable salt thereof.

6. The process according to claim 3 which comprises administering (−)-2-amino-2',6'-propionoxylidide or a therapeutically acceptable salt thereof.

7. The process according to claim 3 which comprises administering 2-amino-N-ethyl-2',6'-propionoxylidide of a therapeutically acceptable salt thereof.

8. The process according to claim 3 which comprises administering 2-amino-2',6'-butyroxylidide or a therapeutically acceptable salt thereof.

9. The process according to claim 3 which comprises administering 2-amino-2'-ethyl-6'-methylpropionanilide or a therapeutically acceptable salt thereof.

10. The process according to claim 3 which comprises administering 2-amino-N-methyl-2',6'-acetoxylidide or a therapeutically acceptable salt thereof.

11. The process according to claim 3 which comprises administering 2-amino-N-methyl-2',6'-propionoxylidide or a therapeutically acceptable salt thereof.

12. The process according to claim 3 which comprises administering 2-amino-N-ethyl-2',6'-acetoxylidide or a therapeutically acceptable salt thereof.

13. The process according to claim 3 which comprises administering 3-amino-2',6'-propionoxylidide or a therapeutically acceptable salt thereof.

14. The process according to claim 3 which comprises administering 3-amino-2',6'-butyroxylidide or a therapeutically acceptable salt thereof.

15. The process according to claim 3 which comprises administering 3-amino-2'-ethyl-6'-methylpropionanilide or a therapeutically acceptable salt thereof.

16. The process according to claim 3 which comprises administering 2-amino-2',6'-diethylpropionanilide or a therapeutically acceptable salt thereof.

17. The process according to claim 3 which comprises administering 3-amino-2-methyl-2',6'-propionoxylidide or a therapeutically acceptable salt thereof.

18. The process according to claim 3 which comprises administering 3-amino-2',4',6'-propionomesidide or a therapeutically acceptable salt thereof.

19. The process according to claim 3 which comprises administering 3-amino-2',6'-dimethyl-4'-propoxypropionanilide or a therapeutically acceptable salt thereof.

20. The process according to claim 3 which comprises administering 2-amino-4'-butoxy-2',6'-dimethylpropionanilide or a therapeutically acceptable salt thereof.

21. The process according to claim 3 which comprises administering 2-amino-2',6'-dimethyl-4'-propoxypropionanilide or a therapeutically acceptable salt thereof.

22. The process according to claim 3 which comprises administering 2-amino-2'-methyl-6'-ethyl-acetonanilide or a therapeutically acceptable salt thereof.

23. The process according to claim 3 which comprises administering 2-amino-2',6'-diethyl-acetonanilide or a therapeutically acceptable salt thereof.

24. The process according to claim 3 which comprises administering 3-amino-2',3',6'-trimethyl-propionanilide or a therapeutically acceptable salt thereof.

25. The process according to claim 3 which comprises administering 2-amino-2-methyl-2',6'-propionoxylidide or a therapeutically acceptable salt thereof.

26. The process according to claim 3 which comprises administering 3-amino-2'-methyl-6'-ethyl-butyranilide or a therapeutically acceptable salt thereof.

27. The process according to claim 3 which comprises administering 3-amino-2',4',6'-butyromesidide or a therapeutically acceptable salt thereof.

28. The process according to claim 3 which comprises administering 3-amino-2',3',6'-trimethyl butyroanilide or a therapeutically acceptable salt thereof.

29. The process according to claim 3 which comprises administering 3-amino-2',6'-valeroxylidide or a therapeutically acceptable salt thereof.

30. The process according to claim 3 which comprises administering 3-amino-3-methyl-2',6'-butyroxylidide or a therapeutically acceptable salt thereof.

31. The process according to claim 3 which comprises administering 3-amino-2-methyl-2',6'-butyroxylidide or a therapeutically acceptable salt thereof.

32. The process according to claim 3 which comprises administering 3-amino-2',6'-dimethoxybutyranilide or a therapeutically acceptable salt thereof.

33. The process according to claim 3 which comprises administering 2-amino-2',6'-diethoxyacetanilide or a therapeutically acceptable salt thereof.

34. The process according to claim 3 which comprises administering 2-amino-N-propyl-2',6'-acetoxylidide or a therapeutically acceptable salt thereof.

35. The process according to claim 3 which comprises administering 3-amino-2'-chloro-6-methylbutyranilide or a therapeutically acceptable salt thereof.

36. The process according to claim 3 which comprises administering 3-amino-4'-methoxy-2',6'-dimethylbutyranilide or a therapeutically acceptable salt thereof.

37. The process according to claim 3 which comprises administering 3-amino-4'-ethoxy-2',6'-dimethylbutyranilide or a therapeutically acceptable salt thereof.

38. The process according to claim 3 which comprises administering 2-amino-2-,6'-dichloropropionanilide or a therapeutically acceptable salt thereof.

39. A pharmaceutical preparation for the suppression of cardiac arrhythmias in mammals comprising as an active ingredient an amount effective for the suppression of cardiac arrhythmias of a compound selected from the group consisting of 2-amino-2',6'-propionoxylidide; (+)-2-amino-2',6'-propionoxylidide; (−)-2-amino-2',6'-propionoxylidide;
2-amino-2'-ethyl-6'-methylpropionanilide;
2-amino-N-methyl-2',6'-propionoxylidide;
3-amino-2',6'-butyroxylidide;
2-amino-2',6'-diethylpropionanilide;
3-amino-2',4',6'-propionomesidide;
2-amino-4'-butoxy-2',6'-dimethylpropionanilide;
3-amino-2'-methyl-6'-ethyl-butyranilide;
3-amino-2',4',6'-butyromesidide;
3-amino-2',6'-valeroxylidide; and therapeutically acceptable salts thereof, together with a pharmaceutically acceptable carrier.

40. The pharmaceutical preparation according to claim 39 which comprises the compound 2-amino-2',6'-propionoxylidide or a therapeutically acceptable salt thereof, together with a pharmaceutically acceptable carrier.

41. The pharmaceutical preparation according to claim 39 which comprises the compound (+)-2-amino-2',6'-propionoxylidide or a therapeutically acceptable salt thereof, together with a pharmaceutically acceptable carrier.

42. The pharmaceutical preparation according to claim 39 which comprises the compound (−)-2-amino-2',6'-propionoxylidide or a therapeutically acceptable salt thereof, together with a pharmaceutically acceptable carrier.

43. The pharmaceutical preparation according to claim 39 which comprises the compound 2-amino-2'-ethyl-6'-methylpropionanilide or a therapeutically acceptable salt thereof, together with a pharmaceutically acceptable carrier.

44. The pharmaceutical preparation according to claim 39 which comprises the compound 2-amino-N-methyl-2',6'-propionoxylidide or a therapeutically acceptable salt thereof, together with a pharmaceutically acceptable carrier.

45. The pharmaceutical preparation according to claim 39 which comprises the compound 3-amino-2',6'-butyroxylidide or a therapeutically acceptable salt thereof, together with a pharmaceutically acceptable carrier.

46. The pharmaceutical preparation according to claim 39 which comprises the compound 2-amino-2',6'-diethylpropionanilide or a therapeutically acceptable salt thereof, together with a pharmaceutically acceptable carrier.

47. The pharmaceutical preparation according to claim 39 which comprises the compound 3-amino-2',4',6'-propionomesidide or a therapeutically acceptable salt thereof, together with a pharmaceutically acceptable carrier.

48. The pharmaceutical preparation according to claim 39 which comprises the compound 2-amino-4'-butoxy-2',6'-dimethylpropionanilide or a therapeutically acceptable salt thereof, together with a pharmaceutically acceptable carrier.

49. The pharmaceutical preparation according to claim 39 which comprises the compound 3-amino-2'-methyl-6'-ethyl-butyranilide or a therapeutically acceptable salt thereof, together with a pharmaceutically acceptable carrier.

50. The pharmaceutical preparation according to claim 39 which comprises the compound 3-amino-2',4',6'-butyromesidide or a therapeutically acceptable salt thereof, together with a pharmaceutically acceptable carrier.

51. The pharmaceutical preparation according to claim 39 which comprises the compound 3-amino-2',6'-valeroxylidide or a therapeutically acceptable salt thereof, together with a pharmaceutically acceptable carrier.

* * * * *

UNITED STATES PATENT AND TRADEMARK OFFICE
CERTIFICATE OF CORRECTION

PATENT NO. : 4,218,477
DATED : August 19, 1980
INVENTOR(S) : Robert N. Boyes, et al It is certified that error appears in the above-identified patent and that said Letters Patent is hereby corrected as shown below:

First page, Item 60, 4th line, "107,031" should read --167,031--;

Col. 9, between lines 29 and 55, that portion of the middle formula reading

" 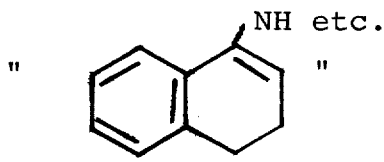 "      should read

-- 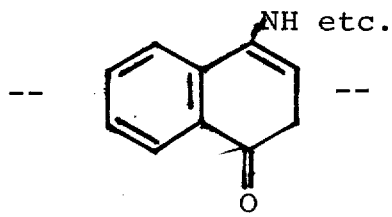 --

Col. 20, line 67, "would" should read --could--;

Col. 24, TABLE 1, the corrected table is attached hereto;

Please correct the location of the captions on TABLE I at Col. 24 so that such table reads as follows:

TABLE I

ACUTE ORAL TOXOCITY AND ANTIFIBRILLATORY EFFECTS IN MICE

| DRUGS | 24 Hr. MORTALITY (mg/kg) | | PROPORTION OF MICE IN EACH GROUP PROTECTED AGAINST FIBRILLATION AT $LD_{0.1}$ (TIME OF ADMINISTRATION OF DRUG BEFORE $CHCl_3$ CHALLENGE) (MINS) | | | | | | PROPORTION OF MICE IN EACH GROUP HAVING ATAXIA JUST BEFORE $CHCl_3$ CHALLENGE (TIME OF ADMINISTRATION OF DRUG BEFORE $CHCl_3$ CHALLENGE) | | | | | |
|---|---|---|---|---|---|---|---|---|---|---|---|---|---|---|
| | $LD_{50}$ | $LD_{0.1}$ | 5 | 10 | 20 | 40 | 80 | 160 | 5 min | 10 min | 20 min | 40 min | 80 min | 160 min |
| QUINIDINE* | 382 | 348 | – | – | 10/10 | 9/9 | 9/9 | – | – | – | 0/10 | 2/10 + 1 death | 9/9(mild) +1 death | – |
| PROCAINAMIDE** | 643 | 248 | 0/10 | 1/10 | 0/10 | – | – | – | 0/10 | 0/10 | 0/10 | – | – | – |
| LIDOCAINE** | 224 | 154 | – | 9/10 | 10/10 | 7/10 | 0/10 | – | – | 0/10 | 9/10 | 0/10 | 0/10 | – |
| 2-AMINO-2',6'-PROPIONOXYLI-DIDE** | 529 | 382 | – | – | 9/10 | 9/10 | 10/10 | 9/10 | – | – | 10/10 | 10/10 | 8/10 | 5/10 |

\* as sulfate salt

\*\* as sulfate salt

UNITED STATES PATENT AND TRADEMARK OFFICE
CERTIFICATE OF CORRECTION

PATENT NO. : 4,218,477
DATED : August 19, 1980
INVENTOR(S) : Robert N. Boyes, et al It is certified that error appears in the above-identified patent and that said Letters Patent is hereby corrected as shown below:

Col. 25, line 59,  "ether" should read --other--;

Col. 26, line 58,  "statistical means" should read --statistical mean--;

Col. 27, line 25,  "propion-" should read --propiono- --;

Col. 27, line 28,  "6'dimethyl-4'" should read --6'-dimethyl-4'- --;

Col. 28, line 61,  "does" should read --dose--;

Col. 29, line 48,  "the optically ..." should start on a new line;

Col. 30, line 44,  "dimethylbutranilide" should read --dimethylbutyranilide--;

Col. 32, line 11,  "-6-" should read -- -6'- --.

Signed and Sealed this

Twenty-first Day of May 1985

[SEAL]

Attest:

DONALD J. QUIGG

Attesting Officer   Acting Commissioner of Patents and Trademarks